(12) United States Patent
Geromanos et al.

(10) Patent No.: US 9,810,669 B2
(45) Date of Patent: Nov. 7, 2017

(54) TECHNIQUES FOR QUANTIFICATION OF SAMPLES

(71) Applicant: Waters Technologies Corporation, Milford, MA (US)

(72) Inventors: Scott J. Geromanos, Middletown, NJ (US); Johannes P C Vissers, Huizen (NL); James I. Langridge, Sale (GB)

(73) Assignee: Waters Technologies Corporation, Milford, MA (US)

(*) Notice: Subject to any disclaimer, the term of this patent is extended or adjusted under 35 U.S.C. 154(b) by 215 days.

(21) Appl. No.: 14/360,395

(22) PCT Filed: Nov. 16, 2012

(86) PCT No.: PCT/US2012/065441
§ 371 (c)(1),
(2) Date: May 23, 2014

(87) PCT Pub. No.: WO2013/081852
PCT Pub. Date: Jun. 6, 2013

(65) Prior Publication Data
US 2014/0330524 A1    Nov. 6, 2014

Related U.S. Application Data

(60) Provisional application No. 61/564,036, filed on Nov. 28, 2011.

(51) Int. Cl.
| | | |
|---|---|---|
| *G01N 33/48* | (2006.01) | |
| *G01N 30/72* | (2006.01) | |
| *H01J 49/00* | (2006.01) | |
| *G01N 33/68* | (2006.01) | |
| *G01N 33/92* | (2006.01) | |
| *G06G 7/58* | (2006.01) | |

(52) U.S. Cl.
CPC ......... *G01N 30/7206* (2013.01); *G01N 33/68* (2013.01); *G01N 33/92* (2013.01); *H01J 49/0036* (2013.01); *F04C 2270/041* (2013.01); *G01N 30/7233* (2013.01)

(58) Field of Classification Search
CPC ........... G06F 19/18; G06F 19/22; G06F 19/24
See application file for complete search history.

(56) References Cited

U.S. PATENT DOCUMENTS

| | | |
|---|---|---|
| 6,717,130 B2 | 4/2004 | Bateman et al. |
| 8,271,207 B2 | 9/2012 | Geromanos et al. |
| 2006/0219889 A1 | 10/2006 | Shvartsburg et al. |
| 2009/0306901 A1 | 12/2009 | Geromanos et al. |
| 2010/0227352 A1 | 9/2010 | Hunter |
| 2010/0261279 A1 | 10/2010 | Ranish et al. |
| 2010/0299076 A1 | 11/2010 | Kajihara et al. |
| 2011/0226941 A1 | 9/2011 | Gorenstein et al. |
| 2011/0260049 A1 | 10/2011 | Geromanos et al. |

FOREIGN PATENT DOCUMENTS

| | | |
|---|---|---|
| WO | WO 2007/140327 A2 | 12/2007 |
| WO | WO 2009/040534 A1 | 4/2009 |

OTHER PUBLICATIONS

International Preliminary Report on Patentability dated Jun. 12, 2014.
J-H Baek, et al., "Multiple Products Monitoring as a Robust Approach for Peptide Quantification," Journal of Proteome Research, vol. 8, No. 7, May 26, 2009, pp. 3625-3632, XP055199842, ISSN: 1535-3893, DOI: 10.1021/pr800853k.
Bruno Domon, et al., "Mass Spectrometry and Protein Analysis," Science, vol. 312, No. 5771, Apr. 14, 2006, pp. 212-217, XP055037340, ISSN: 0036-8075, DOI: 10.1126/science.1124619.
Scott J. Geromanos, et al., "The detection, correlation, and comparison of peptide precursor and product ions from data independent LC-MS with data dependant LC-MS/MS," Proteomics 2009, vol. 9, No. 6, Mar. 1, 2009, pp. 1683-1695, XP002682651, ISSN: 1615-9853, DOI 10.1002/PMIC.200800562.
International Search Report and Written Opinion dated Feb. 5, 2013.

*Primary Examiner* — Eric S Dejong
(74) *Attorney, Agent, or Firm* — Muirhead and Saturnelli, LLC

(57) ABSTRACT

Techniques are described for quantification of molecules in a sample. Mass spectrometry is performed to obtain ionization intensities for precursor and product ions originating from a particular molecule. A first stet of precursor ions having the highest ionization intensities and originating from the particular molecule is determined. For each of the one or precursors in the first set, determined is a second set of one or more product ions that are fragments associated with said each precursor and have the highest ionization intensities of product ions associated with said each precursor. An intensity sum is calculated for the particular molecule by adding ionization intensities of product ions included in the second sets for the one or more precursors in the first set. The intensity sum is compared to information included in a calibration standard. A quantity of the particular molecule in the sample is determined based on said comparing.

37 Claims, 15 Drawing Sheets

| Calibration standard table 760 | |
|---|---|
| Sum of 9 product intensities (e.g., top 3 product ionization intensities for each of the top 3 precursor ionization intensities | Molar amount |
| SUM 1 | 200 fmol |
| SUM2 | 300 fmol |
| SUM3 | 400 fmol |

FIGURE 8

TECHNIQUES FOR QUANTIFICATION OF SAMPLES

REFERENCE TO RELATED APPLICATION(S)

This application is a National Stage of International Application No. PCT/US2012/065441, filed Nov. 16, 2012, which claims priority to U.S. Provisional Application No. 61/564,036, filed Nov. 28, 2011, all of which are incorporated by reference herein.

TECHNICAL FIELD

This application generally relates to techniques for use with analyses of compounds, and, more particularly, to quantification of proteins and other small and large molecules by performing sample analysis using mass spectrometry.

BACKGROUND INFORMATION

Mass spectrometry (MS) is used widely for identifying and quantifying molecular species in a sample. During analysis, molecules from the sample are ionized to form ions and are subsequently separated by m/z using a mass analyser. The separated ions are detected. For each such ion, a signal is produced relating to the mass of the molecule and the charge carried on the molecule. From these ion arrival events, a mass-to-charge ratio (m/z) for each of the ions is determined.

A chromatographic separation technique may be performed prior to injecting the sample into a mass spectrometer. Chromatography is a technique for separating compounds, such as those held in solution, where the compounds will exhibit different affinity for a separation medium in contact with the solution. As the solution flows through such an immobile medium, the compounds separate from one another. Common chromatographic separation instruments include gas chromatographs (GC) and liquid chromatographs (LC). When coupled to a mass spectrometer, the resulting systems are referred to as GC/MS or LC/MS systems. GC/MS or LC/MS systems are typically on-line systems in which the output of the GC or LC is coupled directly to the MS. In an LC/MS system, a sample is injected into the liquid chromatograph at a particular time. The liquid chromatograph causes the sample to elute over time resulting in an eluent that exits the liquid chromatograph. The eluent exiting the liquid chromatograph is continuously introduced into the ionization source of the mass spectrometer. As the separation progresses, the composition of the mass spectrum generated by the MS evolves and reflects the changing composition of the eluent.

Typically, at regularly spaced time intervals, a computer-based system samples and records the spectrum. The response (or intensity) of an ion is the height or area of the peak as may be seen in the spectrum. The spectra generated by conventional LC/MS systems may be further analyzed. Mass or mass-to-charge ratio estimates for an ion are derived through examination of a spectrum that contains the ion. Retention time estimates for an ion are derived by examination of a chromatogram that contains the ion.

Two stages of mass analysis (MS/MS also referred to as tandem mass spectrometry) may also be performed. One particular mode of MS/MS is known as product ion scanning (and is also utilized in data dependent analysis (DDA)) where parent or precursor ions of a particular m/z value are selected in the first stage of mass analysis by a first mass filter/analyzer. The selected precursor ions are then passed to a collision cell where they are fragmented to produce product or fragment ions. The product or fragment ions are then mass analyzed by a second mass filter/analyzer to obtain a resulting product spectrum. The foregoing process can be repeated for other selected precursor ions of interest.

SUMMARY OF THE INVENTION

In accordance with one aspect of the invention is a method for quantification of proteins in a sample comprising: performing sample analysis including liquid chromatography and mass spectrometry to obtain ionization intensities for precursor ions and product ions originating from a particular protein in the sample; determining a first set of M precursor ions originating from the particular protein, wherein the first set of M precursor ions have the M highest ionization intensities of the precursor ions originating from the particular protein; determining, for each of the M precursors in the first set, a second set of N product ions that are fragments associated with said each precursor, wherein the second set of N product ions have the N highest ionization intensities of product ions that are fragments associated with said each precursor; calculating an intensity sum for the particular protein by adding ionization intensities of product ions included in the second sets for the M precursors in the first set; comparing the intensity sum for the particular protein to information included in a calibration standard; and determining a quantity of the particular protein in the sample based on said comparing. The calculating may further include determining M product intensity sums, one of said M product intensity sums being determined for each of the M precursor ions of the first set by adding the N highest ionization intensities for the N product ions included in the second set for said each precursor; and determining said intensity sum by adding said M product intensity sums. M may be equal to or greater than 3. N may be equal to or greater than 3. The method may also include performing first processing including: obtaining a calibration standard mixture including a known concentration or quantity of a predetermined protein; performing sample analysis including liquid chromatography and mass spectrometry to obtain ionization intensities for precursor ions and product ions originating from the predetermined protein in the calibration standard mixture; determining a third set of M precursor ions originating from the predetermined protein, wherein the third set of M precursor ions have the M highest ionization intensities of the precursor ions originating from the predetermined protein; determining, for each of the M precursor ions in the third set for the predetermined protein, a fourth set of N product ions that are fragments associated with said each precursor, wherein the fourth set of N product ions have the N highest ionization intensities of product ions that are fragments associated with said each precursor; calculating an intensity sum for the predetermined protein by adding ion intensities of product ions included in the fourth sets for the M precursors in the third set; storing a set of values included in the calibration standard, the set of values including a first value denoting the known concentration or quantity of the predetermined protein and a second value denoting the intensity sum for the predetermined protein. The first processing may be repeated for the predetermined protein using a plurality of different known concentrations of the predetermined protein. The first processing may be repeated for one or more additional predetermined proteins. The calculating of the intensity sum for the predetermined protein may further include determining M product intensity sums for the predetermined protein, one of said M product intensity sums for the predetermined protein being determined for each of the M precursor ions of the third set for the predetermined protein by adding the N highest ionization intensities for the N product ions included in the fourth set for said each precursor; and determining said intensity sum for the predetermined protein by adding said M product intensity sums for the predetermined protein. The calibration standard may include a first plurality of value sets, each of the first plurality of value sets obtained by performing sample analysis of a calibration standard mixture including a known concentration of a predetermined protein, said sample analysis including performing liquid chromatography and mass spectrometry, each of said values sets included in the first plurality comprising a first value denoting a known concentration of the predetermined protein and a second value denoting a first sum of an M highest ionization intensities for precursor ions originating from the predetermined protein at the known concentration. The method may include adjusting any of the first sum of plurality of sets of values of the calibration standard and the intensity sum when determining the quantity of the particular protein. The calibration standard may include first information about precursor ion intensities at known concentrations for one or more predetermined proteins and second information about product ion intensities at known concentrations for one or more predetermined proteins. The first information of the calibration table may be used in said comparing when an abundance of the particular protein in the sample, as indicated by precursor ion intensities of precursor ions originating from the particular protein, is not expected to exceed an upper bound of a detection limit of a mass spectrometer used to perform the mass spectrometry, and otherwise the second information of the calibration table may be used in said comparing. The quantity of the particular protein may be a molar amount.

In accordance with another aspect of the invention is a method for performing quantification of proteins in a sample comprising: performing sample analysis including liquid chromatography and mass spectrometry to obtain ionization intensities for precursor ions and product ions originating from a plurality of different proteins at varying concentrations in the sample; for each of the plurality of different proteins, determining a precursor intensity sum of an N highest ionization intensities associated with N precursors originating from said each protein and determining a product intensity sum by adding an M highest product ionization intensities for each of the N precursors; determining an estimated molar amount of each of the plurality of different proteins using a calibration standard and the precursor intensity sum for said each protein; determining which one or more data points included in a plurality of data points do not exhibit a linear relationship between the estimated molar amounts and the product intensity sums determined for each of the plurality of different proteins, each of said plurality of data points representing the estimated molar amount and the product intensity sum for one of the plurality of different proteins; and for each data point associated with one of the plurality of different proteins that does not exhibit the linear relationship thereby indicating that the estimated molar amount for the one protein does not vary linearly with respect to the product intensity sum for said one protein, using said product intensity sum and said calibration standard to determine an adjusted estimated molar amount of said one protein. The calibration standard may include a plurality of value sets, each of the plurality of value sets obtained by performing sample analysis of a calibration standard mixture including a known concentration of a predetermined protein, said sample analysis including performing liquid chromatography and mass spectrometry, each of said plurality of value sets included in the first plurality comprising a first value denoting a known concentration in terms of a molar amount of the predetermined protein and a second value denoting a first sum of an M highest ionization intensities for precursor ions originating from the predetermined protein at the known concentration. Using the product intensity sum and said calibration standard to determine an adjusted estimated molar amount of said one protein may include adjusting, in accordance with fragmentation efficiency, any of said product intensity sum and one of the first values included in the plurality of value sets of the calibration table. Determining an estimated molar amount of each of the plurality of different proteins using a calibration standard and the precursor intensity sum for said each protein may include comparing the precursor intensity sum to one or more of the second values included in the plurality of value sets of the calibration table. Determining an estimated molar amount for at least one of the plurality of different proteins may include performing interpolation using two of said plurality of value sets in the calibration table. Using the product intensity sum and said calibration standard to determine an adjusted estimated molar amount of said one protein may further include adjusting the product intensity sum in accordance with fragmentation efficiency to determine an adjusted product intensity sum; comparing the adjusted product intensity sum to one of the second values included in a one of the plurality of value sets of the calibration table; and determining the adjusted estimated molar amount using a first value included in the one value set of the calibration table. The sample analysis may include performing digestion processing prior to performing liquid chromatography and mass spectrometry. The digestion processing may include digesting the particular protein into precursor polypeptides through use of one or more enzymes or chemical cleavage. The method may also include performing ion mobility spectrometry.

In accordance with another aspect of the invention is a system for quantification of molecules in a sample comprising: a mass spectrometer to perform mass spectrometry and obtain, from generated data, ionization intensities for one or more precursor ions and one or more product ions originating from a particular molecule in the sample; a computer readable medium comprising code stored thereon for performing processing including: determining a first set of one or more precursor ions originating from the particular molecule, wherein the first set of one or more precursor ions have highest ionization intensities of precursor ions originating from the particular molecule; determining, for each of the one or more precursors in the first set, a second set of one or more product ions that are fragments associated with said each precursor, wherein the second set of one or more product ions have highest ionization intensities of product ions that are fragments associated with said each precursor; calculating an intensity sum for the particular molecule by adding ionization intensities of product ions included in the one or more second sets for the one or more precursors in the first set; comparing the intensity sum for the particular molecule to information included in a calibration standard; and determining a quantity of the particular molecule in the sample based on said comparing. The system may further comprise an instrument that performs liquid chromatography prior to processing by the mass spectrometer. The system may further comprise an instrument that performs ion mobility spectrometry. The sample may be a mixture including a plurality of proteins. The particular molecule may be any of a protein, lipid, metabolite, and an organic molecular species.

In accordance with another aspect of the invention is a method for quantification of molecules in a sample comprising: performing sample analysis including liquid chromatography and mass spectrometry to obtain ionization intensities for precursor ions and product ions originating from a particular molecule in the sample; determining a first set of one or more precursor ions originating from the particular molecule, wherein the first set of one or more precursor ions have highest ionization intensities of the precursor ions originating from the particular molecule; determining, for each of the one or more precursors in the first set, a second set of one or more product ions that are fragments associated with said each precursor, wherein the second set of one or more product ions have highest ionization intensities of product ions that are fragments associated with said each precursor; calculating an intensity sum for the particular molecule by adding ionization intensities of product ions included in the one or more second sets for the one or more precursors in the first set; comparing the intensity sum for the particular molecule to information included in a calibration standard; and determining a quantity of the particular molecule in the sample based on said comparing.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIGS. 7 and 8 are examples illustrating calibration tables as may be created and used in an embodiment in accordance with techniques herein;

DESCRIPTION

Figure 1:
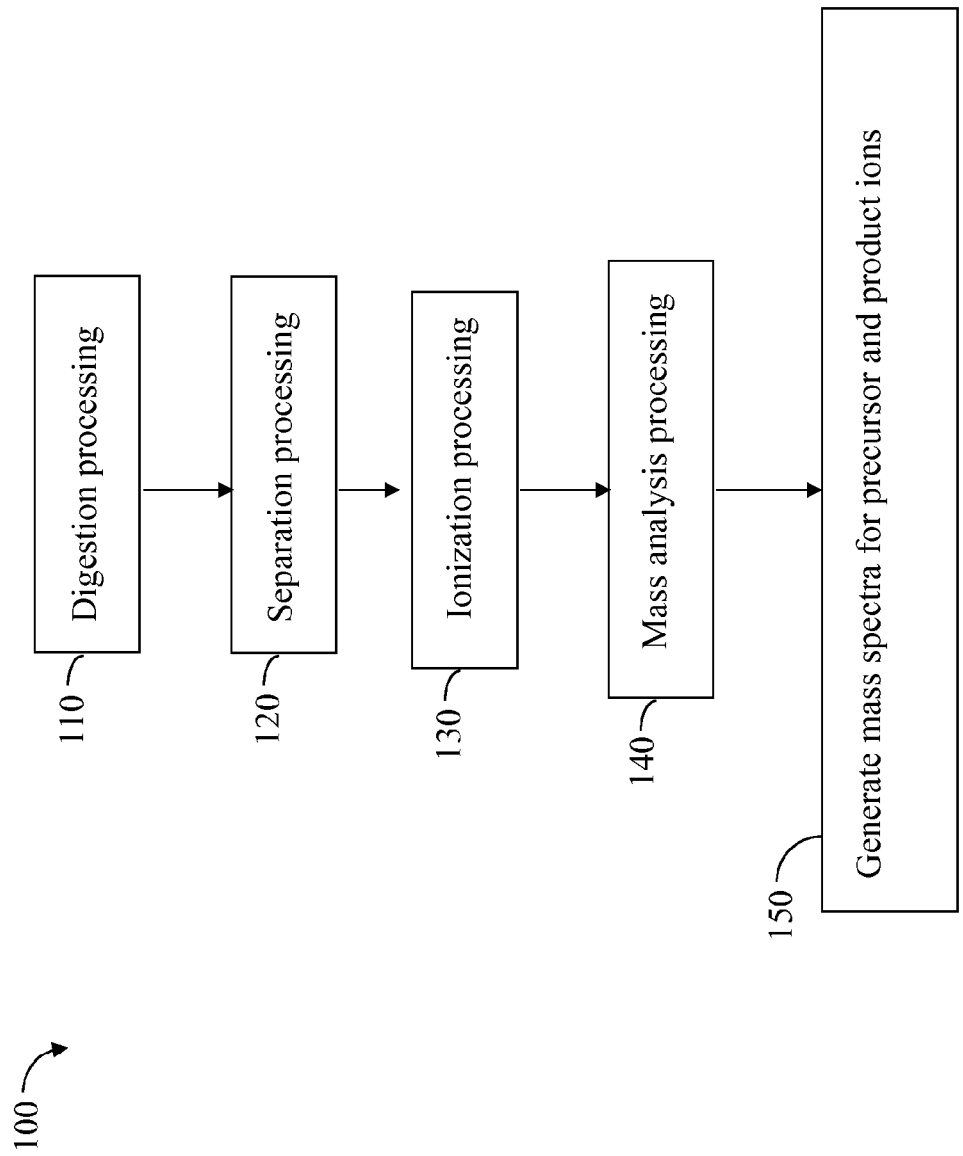
FIG. 1 is a flow diagram of a method for performing chemical analyses of compounds in one embodiment in accordance with the techniques herein.

As used herein, the following terms generally refer to the indicated meanings:

Protein—a specific primary sequence of amino acids assembled as a single polypeptide, or co joined with further polypeptide chains to form a protein.

Peptide—a specific sequence of amino acids assembled as a single polypeptide contained within the primary sequence of a protein.

Tryptic peptides—peptides generated from a protein sequence that result from enzymatic cleavage of the protein by trypsin. In the ensuing description, digest peptides are referred to as tryptic peptides for convenience. It should be understood, however, that embodiments of the present invention apply to other peptide digestion techniques. Moreover, the term "digestion" is used herein to refer generally to any suitable method for degrading or cleaving a polypeptide, including, for example, the use of cellular enzymes (proteases) and intramolecular digestion and chemical cleavage. The term "proteolytic," as used herein, refers to any enzyme which digests or lyses large proteins into smaller sections or amino acids.

Precursor peptides—tryptic peptides (or other protein cleavage products) that are generated using a protein-cleavage protocol. The precursors are optionally separated chromatographically and passed to a mass spectrometer. An ion source ionizes these precursor peptides to typically produce a positively charged, protonated, or multiply protonated, form of the precursor. The mass of such positively charged protonated precursor ions can be deconvoluted and is such herein referred as the "mwHPlus" or "MH+" of the precursor. In the following, the term "precursor mass" refers generally to the protenated, multiply-protonated, mwHPlus or MH+ mass of the ionized, peptide precursor.

Fragments or product ions—Multiple types of fragments or product ions can occur in LC/MS analyses. In the case of tryptic peptide precursors, fragments can include polypetide ions that are produced from, for example collisional induced dissociation (CID), where fragmentation of the intact peptide precursors occurs and whose fragments are indicative of the primary amino acid sequence. This is contained within the originating precursor peptide. Y"-ions and B-ions are examples of such peptide fragments. Fragments of tryptic peptides can also include immonium ions, functional groups such as a phosphate ion ($PO_3$), mass tags cleaved from a specific molecule or class of molecules, or "neutral loss" of water ($H_2O$) or ammonia ($NH_3$), or phosphate ($PO_3^-$) molecules from the precursor.

Y-ions and B-ions—If a peptide fragments at the peptide bond, and if a charge is retained on the N terminal fragment, that fragment ion is termed a b-ion. If the charge is retained on the C terminal fragment, the fragment ion is termed a Y-ion. A more comprehensive list of possible fragments and their nomenclature is provided in Roepstorff and Fohlman, Biomed Mass Spectrom, 1984; 11(11):601 and Johnson et al, Anal. Chem. 1987, 59(21): 2621:2625.

Retention time—in context, typically refers to the point in a chromatographic profile at which an entity reaches its apex or maximum intensity.

Ions—each peptide typically appears in an LC/MS analysis as an ensemble of ions due to the presence of multiply charged ions (ions containing multiple protons or alkali metals) and the natural abundance of the isotopes of the constituent elements. An charged ion has a retention time and an m/z value. The mass spectrometer (MS) detects only ions. The LC/MS technique produces a variety of observed measurements for every detected ion. This includes: the mass-to-charge ratio (m/z), mass (m), the retention time, and the signal intensity of the ion, such as a number of ions counted.

MwHPlus—The neutral, monoisotopic mass of the peptide plus the weight of one proton, 1.007825 amu.

Generally, an LC/MS analysis optionally provides an empirical description of a peptide in terms of its mass, charge, retention time and total intensity. When a peptide elutes from the chromatographic column, it elutes over a specific retention time period and reaches its maximum signal (or apex) at a single retention time. After ionization and (possible) fragmentation, the peptide (and possible fragments) appear as a related set of ions. The different ions in the set correspond to different isotopic compositions and charges of the common peptide. Each ion within the related set of ions produces a single peak retention time and peak shape. Since these ions originate from a common peptide, the peak retention time and peak shape of each ion is identical, within some measurement tolerance. The MS acquisition of each peptide produces multiple ion detections for all isotopes and charge states, all sharing the same peak retention-time and peak shape within some measurement tolerance.

In an LC/MS separation, a single peptide (precursor or fragment) produces many ion detections, which appears as a cluster of ions, at multiple charge states. Deconvolution of these ion detections from such a cluster, indicates the presence of a single entity of a unique monoisotopic mass, at a specific retention time, of a measured signal intensity, in a charge state.

Techniques and embodiments will now be described with reference to exemplary methods and apparatus for analyzing samples such as may be for polypeptide analyses in a system performing mass spectrometry. It will be appreciated that the techniques described herein for use when performing mass spectroscopy may be used in connection with other embodiments and have broader application for analysis of other compounds such as in proteomics, metabonomics, lipidomics, and the like.

Referring to FIG. 1, shown is a flow diagram of a method 100 for performing chemical analyses of compounds as may be performed in an embodiment in connection with the techniques herein. The method 100 includes optionally digesting 110 one or more compounds of a reference sample into component fragments of the compounds, separating 120 the components, ionizing 130 and mass analyzing 140 at least some of the separated components, and generating 150 mass spectra for the precursor and product or fragment ions of at least one compound in the sample. The generated mass spectra may be further analyzed and/or processed for use in connection with any of a variety of techniques for different applications.

As will be described in more detail in following paragraphs, techniques herein may be used to analyze the generated mass spectra data for precursor ions and associated fragments ions in connection with quantifying the one or more proteins included in a sample. The techniques herein may be used to provide for absolute quantification of a particular protein, or proteins, in a sample such as may be expressed in terms of molar amounts.

Some uses of the method 100 are directed toward protein-related analyses. Thus, for convenience, the following description refers to proteins and related fragments, and utilizes examples of analyses of compounds that are polypeptides, such as proteins; in these examples, a protein is digested into component fragments that are precursor fragments of the protein. Precursors, in turn, are ionized to form precursor ions which are then fragmented into product ions in preparation for mass analysis.

Digesting 110 may be an optional step as the techniques herein may be performed using complex mixtures. Step 110 may be accomplished via any suitable technique for cleaving proteins, including known techniques. For example, as described above, a protein is digested into precursor polypeptides or amino acids through use of one or more enzymes such as trypsin. A precursor may be used in additional analyses subsequent to chromatographic separation. As described in more detail below, precursors may be ionized and/or further fragmented into product fragments.

Separating 120 is accomplished by any suitable chromatographic-related technique, including known techniques such as reverse-phase chromatography, gel-permeation chromatography, size-exclusion chromatography, and electrophoresis. Separating 120 provides values associated with retention times of the proteins and/or precursors obtained from digesting 110 proteins in a sample.

In preparation for mass analyzing 140 the eluent from the separating 120 process (e.g., such as a chromatographic separation) is subjected to an ionizing 130 process. Any suitable ionizing 130 process is optionally used, including known techniques such as electrospray ionization and MALDI. During the ionizing 130 process, at least some of the precursors are ionized to form precursor ions. For example, a single protein molecule is digested 110 to form twenty precursor fragments, of which ten are ionized during ionizing 130. As described in more detail below, precursors may be further fragmented to obtain product ions such as through the use of CID in a collision cell, or electron transfer dissociation (ETD) or electron capture dissociation (ECD). It should be noted that there are a variety of different techniques known in the art to induce fragmentation and any such suitable technique may be used although exemplary ones are mentioned herein for purposes of illustration.

Mass analyzing 140 provides values associated with mass and values associated with ion intensity of the precursor ions. Mass analyzing 140 is performed via any suitable mass-analysis techniques, including known techniques. Such techniques include magnetic-sector spectrometry, quadrupole mass spectrometry, ion-trap mass spectrometry, and time-of-flight spectrometry.

As illustrated in step 150, information obtained from the above-described analysis step 140 may be in the form of mass spectra for the precursor and product ions used to obtain an input data set which may be further processed.

In some embodiments performing the steps of FIG. 1, the mass spectra data generated in step 150 may be obtained using an LC/MS system. For example, as described in more detail with reference to FIGS. 2A and 2B, an eluent output by the liquid chromatograph is introduced into a mass spectrometer through an electrospray interface. Optionally, a first quadrupole of a multi-quadrupole MS instrument functions as an ion guide. An alternating voltage is applied to a collision cell (such as 218 of FIG. 2A) of the instrument. Spectra are collected of precursors ions and of their fragment (product) ions, for example, in an alternating fashion, as described below.

Preferably, both precursor ions and associated product ions are formed from the same precursor material obtained from the separating 120 process. In this manner, both precursor ions and associated product ions will have the same retention time data determined from the separating 120 process.

Any suitable method, including known methods, may be used to obtain both precursor and product ions from a single sample injection. Such methods provide effectively simultaneous mass analysis of both precursor and product ions.

For example, a portion of an eluted precursor is fragmented to form product ions, and the precursor and product ions are substantially simultaneously analyzed, either at the same time or, for example, in rapid succession.

As an alternative example, two or more alternating portions of the peak are used respectively for precursor and product analysis. A portion of a peak's precursor material is ionized and analyzed, and then a next portion is dissociated into product fragments that are analyzed. In one embodiment, alternating portions of an eluting precursor are sampled to alternately obtain data for the precursor ion and its product ions. The obtained data permits reconstruction of a peak shape to permit measurement of an accurate retention time value for both the eluted precursor and its associated product. Moreover, for example, peak shape, width, and/or time of reconstructed peaks associated with precursor ions and with product ions are optionally compared to determine which product ions are associated with a particular product ion.

One approach to such alternating, effectively simultaneous analysis, is described in U.S. Pat. No. 6,717,130 to Bateman, et al. ("Bateman"), which is incorporated herein by reference and describes application of an alternating voltage to a collision cell to regulate fragmentation. Thus, an embodiment may use the technique described in the Bateman '130 patent or other suitable technique which may use retention-time observations to support the determination of which product ions are derived from a particular precursor. The product ions are associated with their precursor ion in response to matching retention-time values.

For example, a threshold retention-time difference is selected; if the difference in retention times of a product ion and a precursor ion is less than the threshold value, the product is determined to be derived from the precursor. For example, one suitable threshold value is equal to one tenth the retention-time peak width of the precursor ion. The retention-time value of an ion is optionally defined as the time value of the peak maximum of the peak that was observed for that ion.

Figure 2A:
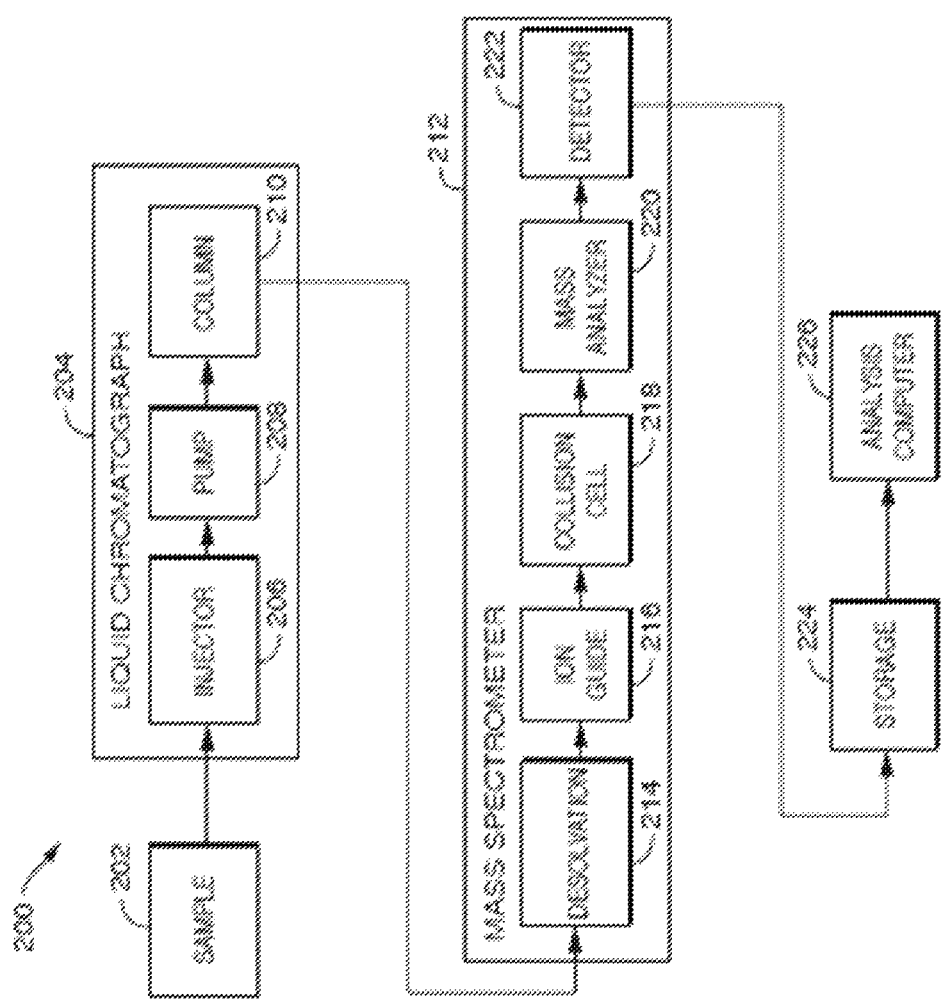
FIG. 2A is a block diagram of an LC/MS system, in accordance with one embodiment in accordance with the techniques herein.
Figure 2B:
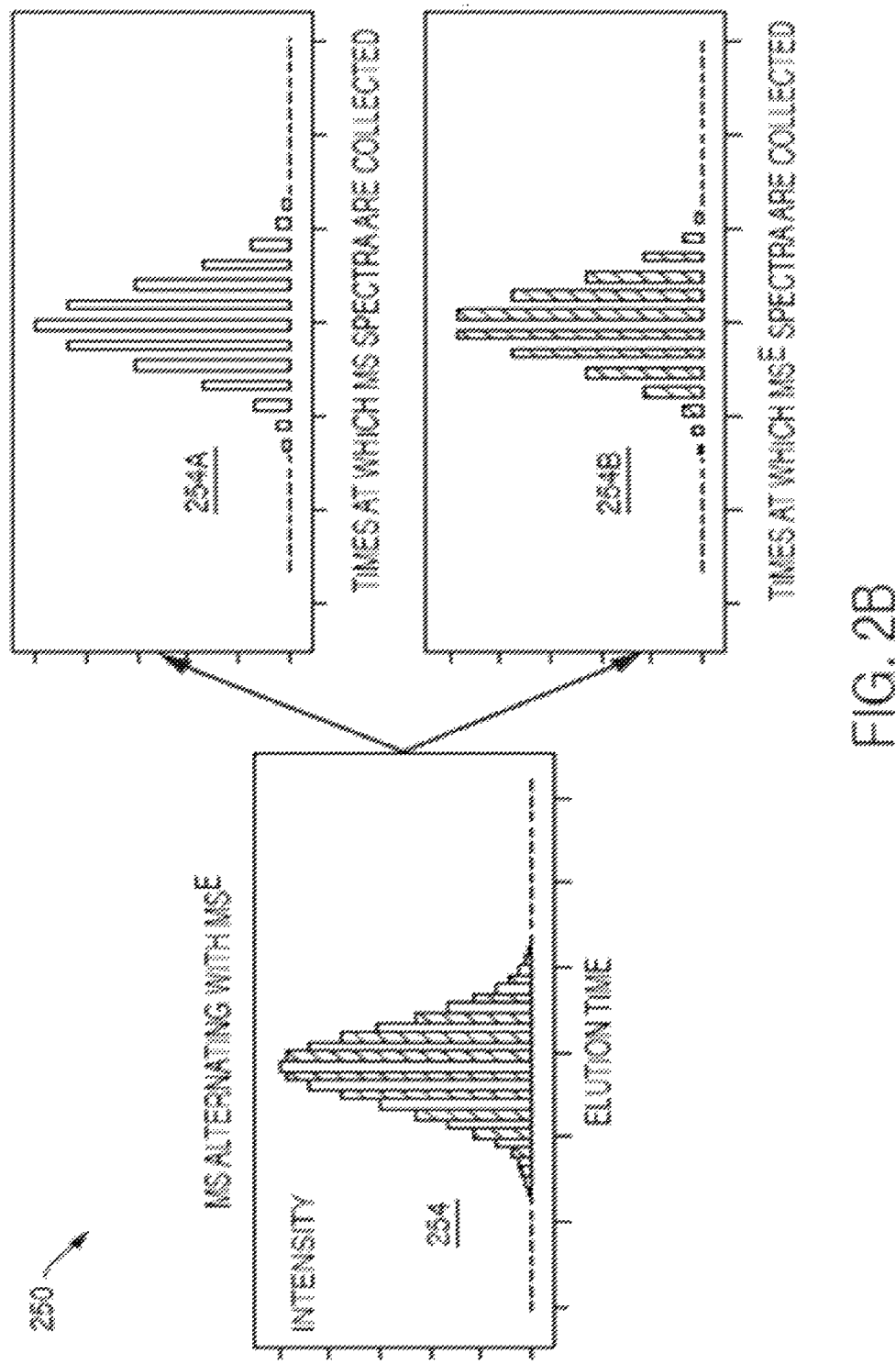
FIG. 2B shows three related graphs, which illustrate the collection of mass spectra in accordance with one embodiment in accordance with the techniques herein.

Referring to FIGS. 2A and 2B, some embodiments of the techniques herein relate to LC/MS instruments. FIG. 2A is a block diagram of an LC/MS system 200, according to one embodiment of the present invention. The instrument includes a chromatography module 204 and a mass-spectrometer module 212 that receives an eluent from the chromatography module 204. The LC module 204 includes an injector 206 that receives a sample 202, a pump 208 and a column 210. The MS module 212 includes a desolvation/ionization device 214, an ion guide 216, a mass analyzer 220, and a detector 222. The system 200 also includes a data storage unit 224 and a computer module 226. In operation, the sample 202 is injected into the LC module 204 via the injector 206. The pump 208 pumps the sample through the column 210 to separate the mixture into component parts according to retention time through the column 210.

The output from the column 210 is input to a mass spectrometer 212 for analysis. Initially, the sample is desolvated and ionized by the desolvation/ionization device 214. Any desolvation technique can be employed, including, for example, a heater, a gas, and a heater in combination with a gas or other desolvation technique. Ionization can be by any suitable ionization technique, including for example, electrospray ionization (ESI), atmospheric pressure chemical ionization (APCI), or other ionization technique. Ions resulting from the ionization are fed to a collision cell 218 by the ion guide 216. The collision cell 218 is used to fragment the ions by any of a variety of known techniques, for example, such as CID, ETD, ECD, or varying combinations of these as known in the art. In some embodiments, the collision cell 218 is operated in a switching mode to support observation of both precursor ions and product ions of the same eluting precursor material.

Any suitable switching techniques may be used, including known techniques. Some embodiments may use a fragmentation protocol in which a relatively simple alternating voltage cycle is applied to the cell 218. This switching is done at a high enough frequency so that multiple elevated and multiple low-energy spectra are contained within a single chromatographic peak. Unlike some other switching protocols, the cycle is independent of the content of the data.

For example, as described in the Bateman '130 patent, an alternating voltage is applied to the collision cell 218 to cause fragmentation. Spectra are collected for the precursors (no collisions) and fragments (results of collisions.) Alternative embodiments may utilize other means for fragmentation.

The output of the collision cell 218 is input to a mass analyzer 220. The mass analyzer 220 is any suitable mass analyzer, including quadrupole, time-of-flight (TOF), ion trap, magnetic sector mass analyzers as well as combinations thereof. The detector 222 detects ions emanating from the mass analyzer 220. The detector 222 is optionally integral with mass analyzer 220. For example, in the case of a TOF mass analyzer, the detector 222 is optionally a microchannel plate detector that counts intensity of ions, i.e., counts numbers of impinging ions. The storage medium 224 provides permanent storage for storing the ion counts for analysis. For example, storage medium 224 is an internal or external computer disk. The analysis computer 226 analyzes the stored data. Data can also be analyzed in real time without requiring storage in a storage medium 224. In that case, the detector 222 passes data to be analyzed directly to computer 226 without first storing it to permanent storage.

The collision cell 218 performs fragmentation of the precursor ions. Fragmentation can be used to determine the sequence of a peptide and subsequently lead to the identity of the originating protein. In the case of CID, the collision cell 218 may utilize an inert gas, such as nitrogen within a pressurized chamber. When a charged peptide interacts with the gas' atoms, the resulting collisions can fragment the peptide by breaking it up at one or more characteristic bonds. The most common resulting fragments are described as Y-or b-ions. Such fragmentation can be accomplished as on-line fragmentation by switching the voltage in a collision cell between a low voltage state (low energy (LE) such as used during an LE scan) which obtains MS spectra of the peptide precursor, with a high voltage state (high or elevated energy (EE) such as used during an EE scan) which obtains MS spectra of the collisionally induced fragments of the precursors. High and low voltages are referred to, respectively, as high or elevated energy and low energy, since a voltage is used to impart kinetic energy to an ion. Such techniques using alternating LE and EE consecutive scans are described in the Bateman '130 patent.

It should be noted that the MS 212 may be any type of spectrometer or configuration of components performing mass spectrometry. For example, the MS 212 may also be, for example, a mass spectrometer by Thermo Fisher Scientific, Inc. using the Orbitrap technology such as the Thermo Scientific LTQ Orbitrap Velos mass spectrometer.

The chromatographic module 204 includes any suitable chromatography instrument(s), including known instruments, such as column-based instruments. Suitable columns include columns known to one having ordinary skill in the chromatographic arts. The column housing material (e.g., serving as the stationary phase) can be formed from, for example, metallic or insulating materials. Suitable materials include known materials such as silica, bonded silica, a hybrid organic inorganic material, and the like. The column can include more than one column, disposed in serial and/or parallel configurations. For example, the column can be a capillary column and can include multiple capillary tubes.

The computer module 226 is in data communication with other components of the system 200 via wired and/or wireless means, such as those known in the data-communication arts. The module 226 receives process data, for example, from the mass-spectrometer module 212, and provides control signals. The module 226 is optionally configured to implement methods described herein, such as the method 100 for chemical analysis described above, and/or the different techniques described herein for further processing the input data set acquired as a result of the step 150 of FIG. 1. The module 226, in various illustrative embodiments, is implemented in software, firmware, and/or hardware (e.g., as an application-specific integrated circuit), and includes, if desired, a user interface. The module 226 includes and/or is in communication with storage component(s), such as the storage unit 224.

Suitable implementations of the module 226 include, for example, one or more integrated circuits, such as microprocessors. A single integrated circuit or microprocessor in some alternative embodiments includes the module 226 and other electronic portions of the system 200. In some embodiments, one or more microprocessors implement software that enables the functions of the module 226. In some embodiments, the software may be executable code which is stored on a computer-readable medium and designed to run on general-purpose equipment and/or specialized processors dedicated to the functionality herein described.

A control means (not shown) provides control signals for the various power supplies (not shown) which respectively provide the necessary operating potentials for the components of the mass spectrometer (e.g., elements 214, 216, 218, 220 and 222). These control signals determine the operating parameters of the instrument, for example the operation of the analyzer 220. The control means is typically controlled by signals from a computer, such as the analysis computer 226, which may also be used to process the mass spectral data acquired. The computer 226 may also display and store mass spectra produced and receive and process commands from an operator. The control means may be automatically set to perform various methods and make various determinations without operator intervention, or may optionally require operator input at various stages.

The control means may also be configured to switch the collision cell 218 back and forth between at least two different modes such as for use in accordance with an alternating LE-EE scanning technique described in the Bateman '130 patent. In a first mode, a relatively high voltage (such as more than 15V) is applied to the collision cell which is sufficient to cause a fair degree of fragmentation of ions passing therethrough. In a second mode a relatively low voltage (such as less than or equal to 5V) is applied which causes relatively little (if any) significant fragmentation of ions passing therethrough. The control means may switch between modes such as approximately every second. As described elsewhere herein, the second mode may be used in connection with generating a spectrum for one or more precursor ions which are then fragmented at a next subsequent point in time when operating in the first mode generating another spectrum of one or more related product ions.

A molecule in an eluent that is separated by a chromatographic separation, and elutes from the column is referred to as the common eluting molecule or originating molecule. As described above, the originating molecule is ionized through the ionization source of the mass spectrometer. The resulting ions are measured in an LC/MS or LC/MS$^E$ spectra. It should be noted that depending on the context, LC/MS may generally refer to the LC/MS process of data acquisition. In connection with data collected and represented such as in the form of spectra, for example, as in connection with FIG. 2B described herein, MS spectra may refer to spectra from unfragmented precursors. MS$^E$ spectra may refer to elevated-energy spectra (i.e., spectra from fragmented precursors, that is, product ions, labeled "MS$^E$". As a result of isotopic composition and or fragmentation processes, each originating molecule can give rise to multiple categories of ions, each having a unique value of mass and charge. The ion corresponding to the originating molecule is termed the precursor ion, or just the precursor.

In peptide digests the originating molecule is a peptide and the ion corresponding to the peptide may also be referred to as the precursor. Any ion derived from the originating molecule, whether the precursor or a fragment, must have the same retention time and chromatographic peak profile as the precursor.

In an LC/MS experiment, an ion can be described and/or referred to by its retention time, mass-to-charge ratio or mass, charge state, and intensity. Such information characterizing an ion may be determined using techniques as described in PCT Publication No. WO2007/140327 published Dec. 6, 2007 (PCT application no. PCT/US07/69784, international filing date May 25, 2007), ION DETECTION AND PARAMETER ESTIMATION FOR N-DIMENSIONAL DATA, Gorenstein et al., which is incorporated by reference herein, where the foregoing information for an ion may be determined with respect to the monoisotopic variation of the ion and its determined apex of a chromatographic peak. A single molecule can appear in an LC/MS chromatogram as a cluster of ions. A peptide gives rise to one or more ion clusters. Each cluster corresponds to a different charge state (e.g., Z=1 or Z=2). Each ion in a cluster corresponds to a different isotopic composition of the peptide. In a cluster of ions from a common peptide, the monoisotope is the ion having the lowest mass, where all the isotopes are in their most abundant, low mass state. Since the ions in the cluster come from a common originating molecule, they must share a common retention time and peak profile.

An originating molecule can give rise to multiple ions due to isotope and charge effects. Additional, important sources of ions are fragments of the originating molecule. These fragments arise from processes that break up the originating molecule. These processes can occur in the ionization source or in a collision cell. Because fragment ions derive from a common eluting, originating molecule, they must have the same chromatographic retention time and peak profile as the originating molecule. The retention time and peak shapes of ions that derive from a common originating molecule are the same because the time of ion formation, fragmentation, and ion detection is generally much shorter then the peak width of the originating molecule. For example, a typical chromatographic peak width, measured at full-width at half-maximum (FWHM) is 5 to 30 seconds. The time of ion formation, fragmentation, and detection is typically sub milliseconds. Thus on a chromatographic time scale, the time of ion formation is an instantaneous process. It follows that differences in observed retention times of the ions that derived from an originating molecule is effectively zero. That is, sub-millisecond retention time differences between ions that derived from an originating molecule are small compared to the chromatographic peak width.

The ions that are associated with an originating molecule fall into one of several categories. An ion derived from an originating molecule can be a precursor, a fragment of the precursor, or a fragment of a fragment, or a neutral loss of any of the above masses. Any of these masses can be seen in one or more discrete isotopic states, and in one or more charge states.

In the case of peptides, a given peptide is generally seen to be a cluster of ions, each in a distinct isotopic state, and each in one or more charge states. Ideally the ionization source produces precursors that are a protonated form of the neutral originating molecule. One or more protons can be attached to the neutral molecule and thus the precursors can be one or more mass units higher than the neutral with charge Z=+1, or +2, etc. In practice, this precursor (termed mwHPlus) may be accompanied by lower mass entities that result from the loss of neutral molecules such as water, ammonia, or phosphate. Fragmentation can occur in the source, yielding, typically, Y— or b-ions. As described in connection with techniques herein, fragmentation can be also be deliberately induced by down-stream interactions with gas molecules in a collision cell. With respect to ions that are generated from collision-induced disassociation of intact precursor ions, the fragment product ions are associated with their parent precursor ion. By using the mass spectrometer in a high-low data acquisition mode (also referred to herein as an elevated-low-data acquisition mode) as described in the Bateman '130 patent, this association is accomplished without requiring the instrument to pre-select a single precursor for subsequent fragmentation. More specifically, associated ions are appropriately grouped when multiple precursors are fragmenting simultaneously, at essentially the same retention time.

The retention time and chromatographic peak profile of a molecule (peptide, metabolite, natural product) eluting from a chromatographic support matrix, such as column 210, is a function of the physical interaction of that molecule between the support matrix and mobile phase. The degree of interaction that a molecule has between the support matrix and the mobile phase dictates the chromatographic profile and retention time for that molecule. In a complex mixture, each molecule is chemically different. As a result, each molecule can have a different affinity for the chromatographic matrix and the mobile phase. Consequently, each can exhibit a unique chromatographic profile. Generally, a chromatographic profile for a specific molecule is unique and describes the physicochemical properties of that molecule. Parameters optionally used to characterize the chromatographic peak profile of a given molecule include the time of initial detection (liftoff), normalized slope, the time of inflection points relative to the time of the peak apex, the time of maximum response (peak apex), the peak width, at inflection points, at full-width-at-half-maximum (FWHM), peak shape asymmetry, and the time of the final detection (touch down) to name only a few.

FIG. 2B shows three related graphs that illustrate the collection of mass spectra during a period of time that covers an eluted peak of a precursor, according to one embodiment of the invention. A first graph 254 illustrates the alternating collection over elution time of low-energy spectra (i.e., spectra from unfragmented precursors, labeled "MS") and elevated-energy spectra (i.e., spectra from fragmented precursors, that is, product ions, labeled "$MS^E$".) Second and third graphs 254A, 254B respectively illustrate the MS and $MS^E$ spectral collection times and the reconstruction of the retention time peak associated with the precursor as may be generated using the alternating scanning technique described in the Bateman '130 patent.

The reconstructed peak represents the chromatographic elution profile of a single precursor. The horizontal axis corresponds to elution time of the peak profile. The vertical axis corresponds to arbitrary units of intensity associated with the time-varying concentration of the precursor as it elutes from the chromatographic column. An eluting precursor, passed to the mass spectrometer, thus produces ions in both low-and elevated-energy modes. The ions produced in the low-energy mode are primarily those of the precursor ions in possibly different isotopic and charge states. In proteomic studies, the precursor ions are peptides generated from enzymatic digestion (typically a tryptic digest) of the intact protein(s). In elevated-energy mode, the ions are primarily different isotopes and charge states of the fragment, or product, ions of those precursors. High-energy mode can also be referred to as elevated-energy mode.

In the graph 254, the alternating white and black bars thus represent the times at which spectra are collected with low and high (or elevated)-energy voltages of the eluting chromatographic peak. The low-energy (LE) graph 254A depicts the times at which a low-energy voltage is applied in the collision cell 218, resulting in low-energy spectra. The high or elevated energy (EE) graph 254B depicts the times at which an elevated-energy voltage is applied in the collision cell 218, resulting in elevated-energy spectra.

In connection with techniques described herein, an embodiment may determine masses of particular precursors of interest using a variety of different techniques. For example, in one embodiment utilizing the Bateman techniques as described elsewhere herein, the low energy (LE) cycle or mode may be used to generate spectra containing ion primarily from unfragmented precursors while the elevated-energy (EE) spectra contain ions primarily from fragmented precursors or product ions.

As mentioned above, the mass spectra data may be utilized in accordance with techniques herein to generally for relative and absolute quantification of proteins and other molecules that may be included in a sample such as a complex mixture. The techniques described herein may be used to quantify organic species such as peptides and/or proteins with the approach also easily and more generally applicable for use with a wide range of organic compounds, such as small molecule metabolites or environmental compounds.

In U.S. patent application Ser. No. 11/914,578, SYSTEM AND METHOD FOR ABSOLUTE QUANTITATION OF PROTEINS USING LC/MS, Geromanos et al., (the '578 application), which is incorporated by reference herein, described is a technique to estimate the absolute quantification of a particular protein using the sum or average of the top N, such as top 3, precursor ion intensities for precursors originating from the particular protein and comparing the foregoing sum or average precursor ion intensity information to information included in a calibration standard table. The calibration standard table may include previously determined sum or average precursor ion intensity information for one or more predetermined proteins at varying abundances such as different concentrations in terms of molar amounts. As described in the '578 application, the relationship between an estimated molar amount of a protein and the sum or average precursor intensity for the top 3 precursors, or more generally top N, precursors for the protein is similar across all proteins and scales in approximately a linear relationship, within some acceptable threshold such as +/−20%. The foregoing linear relationship holds as molar concentrations are varied for the same or different protein. In other words, a calibration standard table may include information regarding the sum or average precursor intensity for the top 3 precursors for one protein at varying molar amounts and this information may be used to estimate the absolute quantity of another different protein based on the foregoing linear relationship. For example, assume the calibration standard includes a first sum precursor intensity for the top 3 precursors of one protein at 1 picomole (pmol) and that a second protein for which quantification is performed has a sum precursor intensity for 3 observed top precursors that is approximately twice the first sum. In this case, the estimated molar amount of the second protein may be determined as 2 pmol based on the linear relationship between the sum of the top 3 precursor ion intensities of a protein and the molar amount of the protein. Thus, the basis of the foregoing approach is to use the parent precursor ion intensity information from the mass spectrometry data to provide information for quantification. For example, in the case of LC-MS$^E$ data this could be the area under the curve for all isotopes and all charge states of a peptide as it elutes. This information is then used as a surrogate of the parent protein intensity.

However, at high concentrations the peptide precursor intensity information obtained via mass spectrometry will become unreliable due to saturation effects (e.g., such as associated with the column and mass spectrometer) and the peptide and hence protein abundance or amount will be underestimated using the techniques described in the '578 patent application. In other words, the above-mentioned linear relationship between estimated molar amounts of a protein and the sum or average of the top N precursors originating from the protein holds true. However when a peptide or precursor is present in amounts at or above the saturation point for a particular system and associated instruments utilized to perform an experiment, the resulting mass spectra data fail to include the correct precursor ion intensity information.

Every mass spectrometer has an upper limit to the magnitude of signal it can measure without saturating its detector. If the signal exceeds this limit, the signal is "clipped" and part of it is lost. Likewise, every mass spectrometer has a lower limit to the magnitude of signal that it can distinguish from electronic and chemical background noise. The ratio of the maximum signal to the minimum signal is the mass spectrometer's dynamic range. Such dynamic range has a significant effect on a mass spectrometer's usability. If an instrument's dynamic range is very narrow, sample preparation becomes more critical and more difficult. It is easy to introduce the wrong amount of sample and either get a clipped signal (too much sample) or no signal (too little sample).

Thus, in one embodiment in accordance with techniques herein, at the onset of saturation of the organic species, the sum of the fragment ion intensities for each peptide or precursor may be used as an approximate measure of the abundance of the peptide or precursor. This follows since the product ions associated with a precursor ion are generally present with much lower ion intensities or signal responses than the precursor ion. The foregoing fragment ion intensities may be correlated back to the parent protein abundance (e.g., fragments to peptides to proteins) and extend the dynamic range over which organic species can be quantified. Therefore, in one embodiment using techniques herein as described in more detail below, at low concentrations peptide precursor information may be used to estimate the molar amount of the protein, whereas at high concentrations fragment ion intensities may be used (e.g., from the elevated energy MS$^e$ data or from product ions information obtained using tandem mass spectrometry).

It should be noted that the saturation limit and, more generally, dynamic range, may vary depending on characteristics of the particular detector of the mass spectrometer. For example, mass spectrometers using a TDC (time to digital converter) detector may achieve saturation at lower concentration levels than mass spectrometers using ADC (analog to digital converter) detectors. Furthermore, an ADC detector's saturation point (upper bound of the dynamic range of MS) may also be further limited or reduced if ion mobility is also utilized. In summary, different factors of a particular system utilized for an experiment may be considered when estimating the dynamic range and where detector saturation occurs thereby assisting in selecting at which point either the precursor or fragment intensities may be used to quantify a mixture or sample known or expected to have a particular concentration range.

The techniques described herein provide for quantitatively profiling mixtures for which sample analysis is performed, such as using LC-MS, from which mass spectra are obtained. An embodiment may use the fragment ion intensity information for fragments originating from a particular protein to estimate the absolute quantity of the particular protein present, such as the molar amount, using calibration tables.

Figure 3:
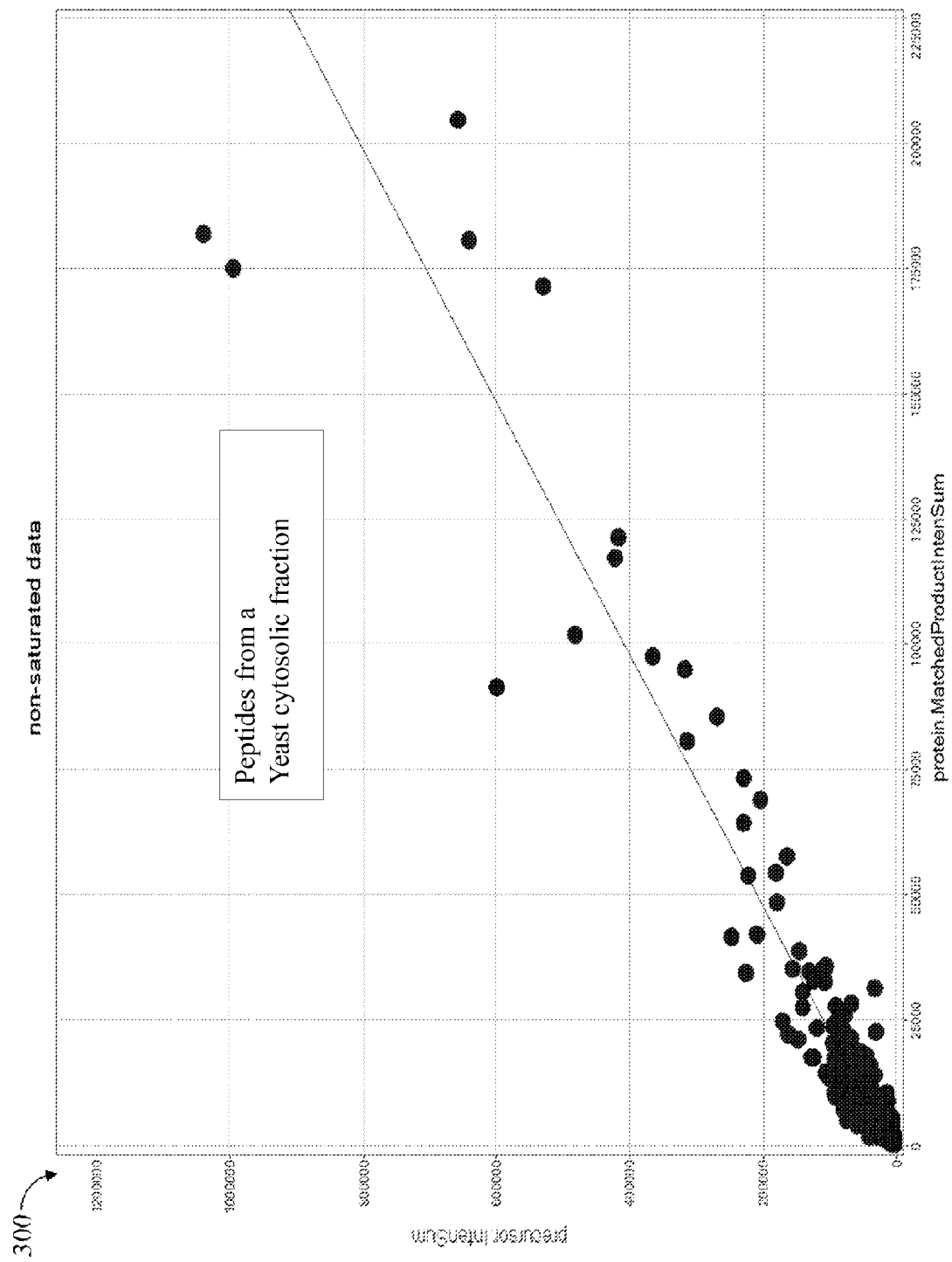
FIG. 3 is a graphical illustration of precursor intensity sums and associated product intensity sums as may be used in an embodiment in accordance with techniques herein.

Referring to FIG. 3, shown is an example graphically illustrating a linear relationship between summed precursor intensities for a protein and the sum of associated product ion intensities for the protein. In this example 300, the inventors ran an LC-MS experiment for a sample of peptides from a yeast cytosolic fraction where the sample includes a mixture of different proteins having different varying concentrations. Each point in the example 300 has a Y-axis coordinate that is the precursor intensity sum of all precursor intensities originating from a particular protein (e.g, summed precursor intensity for all matched peptides to a given protein) and an X-axis coordinate that is the ion intensity sum of all product ions originating from particular protein or associated with foregoing precursors of the particular protein having their sum represented by the Y-axis coordinate. It should be noted that although the foregoing is illustrated using intensity sums with respect to all precursors and all associated product ions for a protein, more generally, the foregoing may also be illustrated using the top N precursor ion intensities for precursors originating from the protein and all product ion intensities associated with those top N precursors. As a further variation, the foregoing may also be illustrated using the top N precursor ion intensities for precursors originating from the protein and the top M product ion intensities associated with those top N precursors. In one embodiment, M and N may be preferably equal to or greater than 3. As a further variation, the foregoing may also be illustrated using the sum of the top N precursor ion intensities for precursors originating from the protein and the sum of all product ion intensities associated with those top N precursors. In connection with the foregoing illustration, it should be noted that the intensity sum may include all charge states and isotopic variations of an ion. The sample used to produce the data illustrated in 300 had known concentrations resulting in precursor and product ion intensities within the dynamic range of the LC-MS system utilized. For mass spectra data analyzed for the sample having ion intensities in the dynamic range (e.g., below saturation), the example 300 illustrates a linear relationship between the various data points thereby representing a linear relationship between summed precursor intensity information and corresponding summed product ion intensity information for different proteins at varying concentrations or abundances.

As described elsewhere herein and known in the art, any suitable technique may be used to analyze the mass spectra data and associate product ions with precursors and precursors with originating protein to obtain the information illustrated in the example 300.

Figure 4:
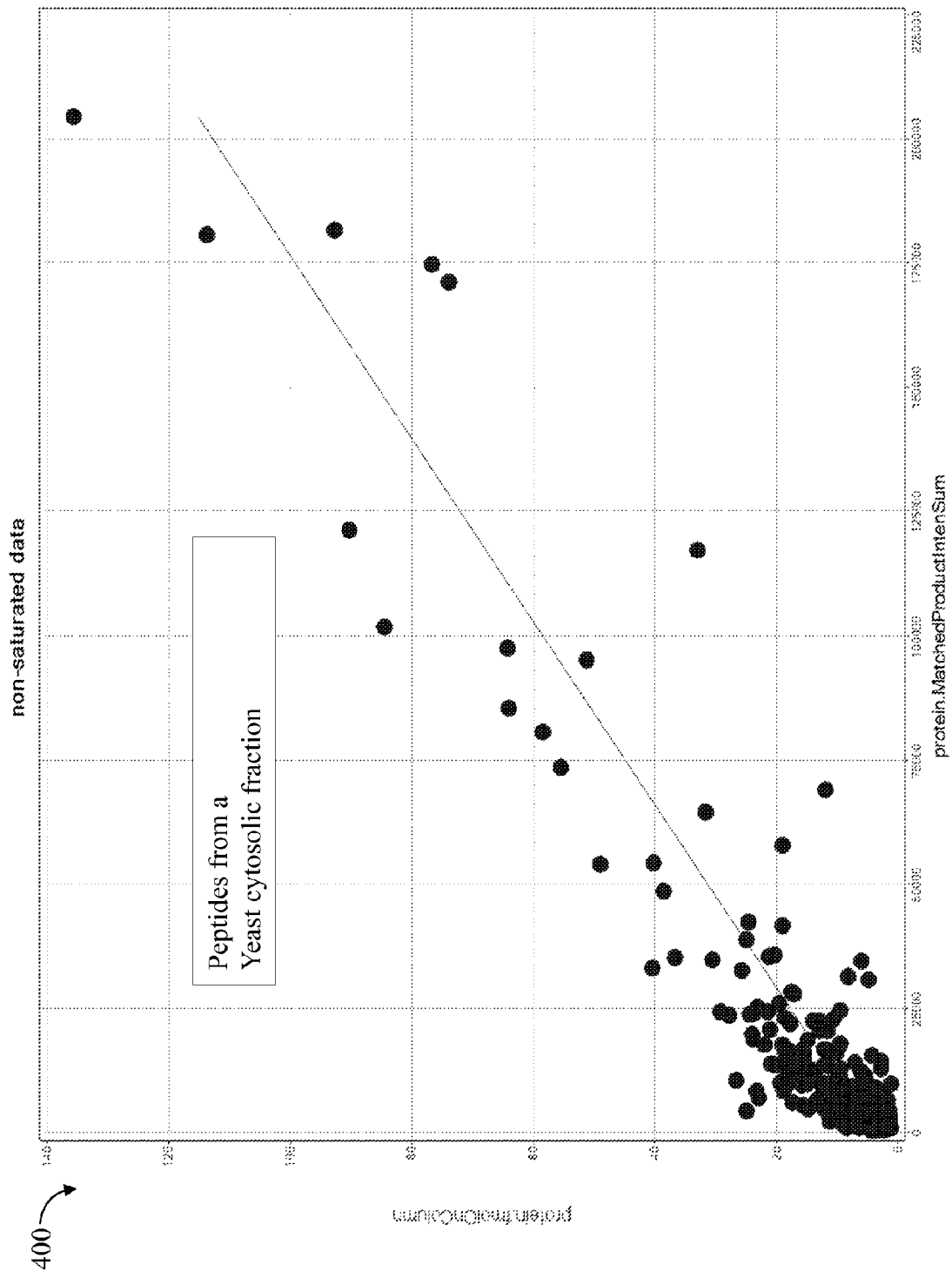
FIGS. 4 and 5 are graphical illustration of estimated amounts of proteins and associated product intensity sums as may be used in an embodiment in accordance with techniques herein.

Referring to FIG. 4, shown is an example graphically illustrating a linear relationship between summed product ion intensities for a protein and the estimated molar amount of the protein. In this example 400, the inventors used the precursor sum intensity for the proteins (as represented by the Y-axis values in FIG. 3) to estimate the molar amount of the protein using a calibration standard as described in the '578 patent application. The foregoing estimated molar amounts for the proteins are illustrated in FIG. 4 as Y-axis values (in terms of fmol or femtomole) plotted against the same respective X-axis values as described above in FIG. 3. For mass spectra data analyzed for the sample having ion intensities in the dynamic range (e.g., below saturation), the example 400 illustrates a linear relationship between the various data points thereby representing a linear relationship between estimated molar amounts of proteins (e.g., where the foregoing estimate is based on the summed precursor intensity information for Y-axis values of FIG. 3) and corresponding summed product ion intensity information for the proteins at varying concentrations or abundances.

Figure 5:
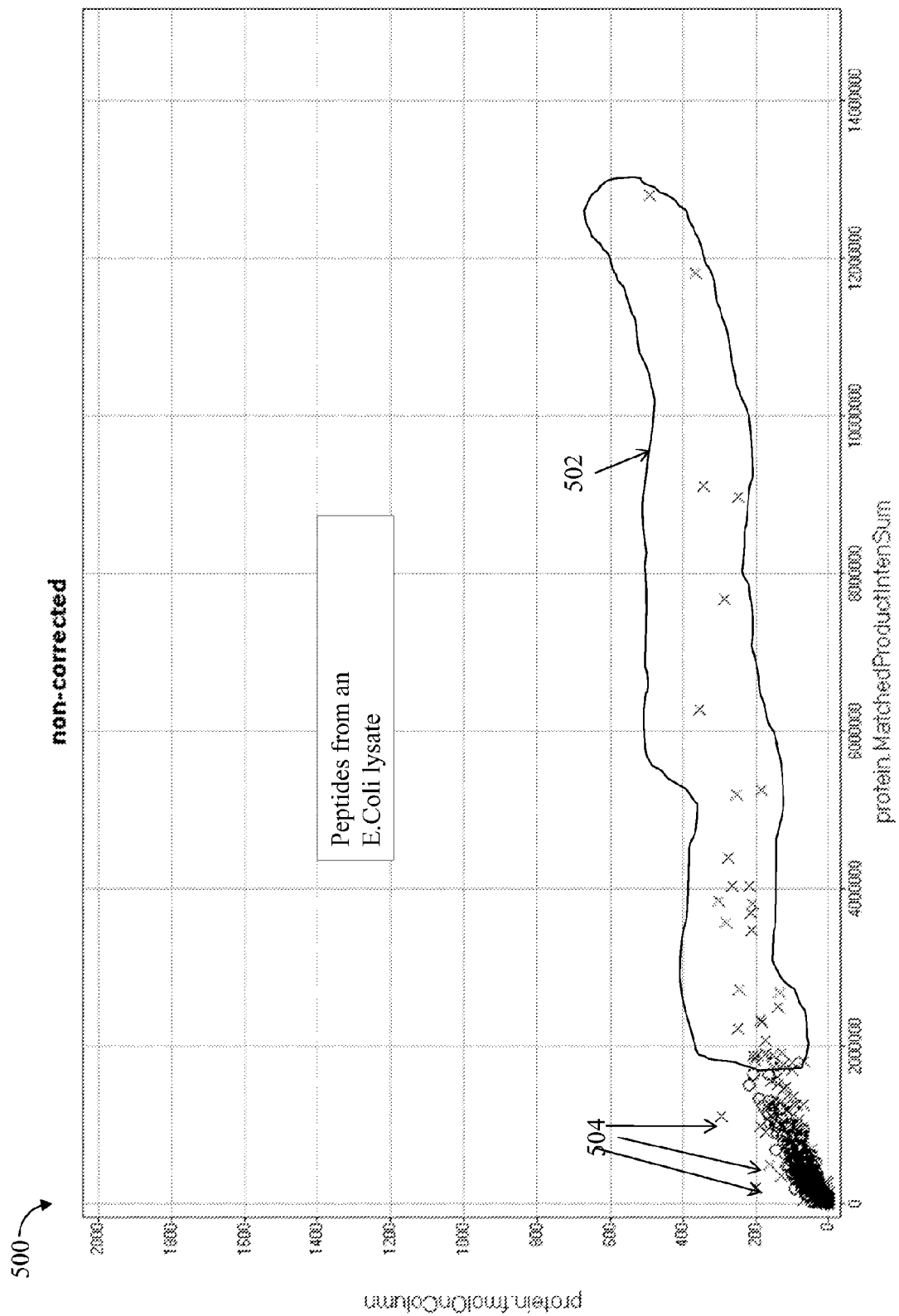

Referring to FIG. 5, shown is an example graphically illustrating summed product ion intensities for a protein plotted against the estimated molar amount of the protein for ion intensities exceeding the dynamic range (e.g., exceeding the saturation limit) of the detector. In this example 500, the inventors ran a single LC-MS experiment with an E. Coli lysate sample having concentrations known to result in ion intensities exceeding the saturation limit. As described above in connection with FIG. 4, the sum of the intensities for all precursors (e.g., precursor sum intensity for all matched peptides) originating from each of the proteins in the sample is used to estimate the molar amount of the protein using a calibration standard as described in the '578 patent application. As described elsewhere herein, the precursor sum intensity used may be, for example, the sum of the top 3 precursor ion intensities originating from each protein. The foregoing estimated molar amounts for the proteins are illustrated in FIG. 5 as Y-axis values (in terms of fmol or femtomole) plotted against respective X-axis values for the sum of the product ionization intensities matched to the particular precursors (e.g., the top 3 precursors) used to estimate the molar amount of the protein. As also described elsewhere herein the sum of the product ionization intensities used in determining X-axis values of FIG. 5 may be, for example, the sum of all such product ions generated from (associated with) the top 3 precursors, or the sum of the top M such product ions associated with the top 3 precursors for the protein.

The example 500 illustrates the non-linearity that occurs when summed precursor intensities for a protein exceeding the saturation limit are used to estimate the molar amount of the protein where such precursor intensities are obtained from the mass spectra data. Element 508 illustrates some of the points that may be characterized as linear thereby providing an indication that such points are associated with precursor intensities within the saturation limit or dynamic range of the detector. In contrast, elements 502 and 504 illustrate some of the points that may be characterized as non-linear thereby providing an indication that such points are associated with precursor intensities exceeding the saturation limit or dynamic range of the detector. Additionally, such a non-linear relationship thereby also provides an indication that such points are associated with precursor intensities obtained from mass spectra data that provide for underestimation as to the actual molar amount of the protein in the sample. In connection with FIG. 5, it should be noted that those points which are determined to be non-linear are denoted by "X" and those remaining points which are determined to otherwise be linear are denoted by "O".

In an embodiment in accordance with techniques herein, if it is determined that the precursor intensity exceeds the detection saturation limit, then the sum of the observed product ion intensities associated with that precursor may be used rather than the observed precursor ion intensity because such observed precursor ion intensity (as obtained from the mass spectra data) is suspect as inaccurate. It should be noted that the foregoing assumes the actual product ion intensities are within the detector limits and therefore accurately reflected in the observed product ion intensities of the mass spectra data.

It may be determined that the precursor intensity exceeds the detection saturation limit in a variety of different ways. One is described above by the determination that a particular point in FIG. 5 is non-linear as may be determined, for example, by visual inspection of the graphical data of FIG. 5 or by mathematical analysis of the data to determine where data exhibits a linear vs. non-linear characteristic. Additionally, the foregoing may also be based on expected dynamic range of an MS system utilized and general knowledge regarding a range of concentrations of proteins in the sample under analysis. In such cases, the product ion intensities associated with the precursors having the top N precursor ionization intensities for a protein may be used to estimate the molar amount of the protein rather than using the observed top N precursor ionization intensities. More specifically, an embodiment may use the techniques described herein in the '578 patent application modified to now substitute the sum of the product ion intensities for each of the precursor intensities used in the '578 application to estimate the molar amount of the protein. For example, 3 precursors—P1, P2 and P3—have the top 3 precursor ionization intensities of precursors originating from protein A. Precursor P1 is associated with product ions F1, F2 and F3 having the top 3 product ionization intensities for P1. Rather than use the observed precursor ionization intensity for P1 as obtained from the mass spectra data when estimating the molar amount of the protein A, the sum of the product ion intensities for F1, F2 and F3 may be used. In a similar manner, rather than use the observed precursor ionization intensities for P2 and P3 as obtained from the mass spectra data when estimating the molar amount of the protein A, the sum of the product ion intensities for those top 3 fragments associated with P2 and P3 may be used. In this manner, the sum ion intensity utilized to estimate the molar amount of protein A is based on a sum of product ionization intensities of product ions originating from protein A and its precursors rather than utilize the precursor ionization intensities.

Figure 6:
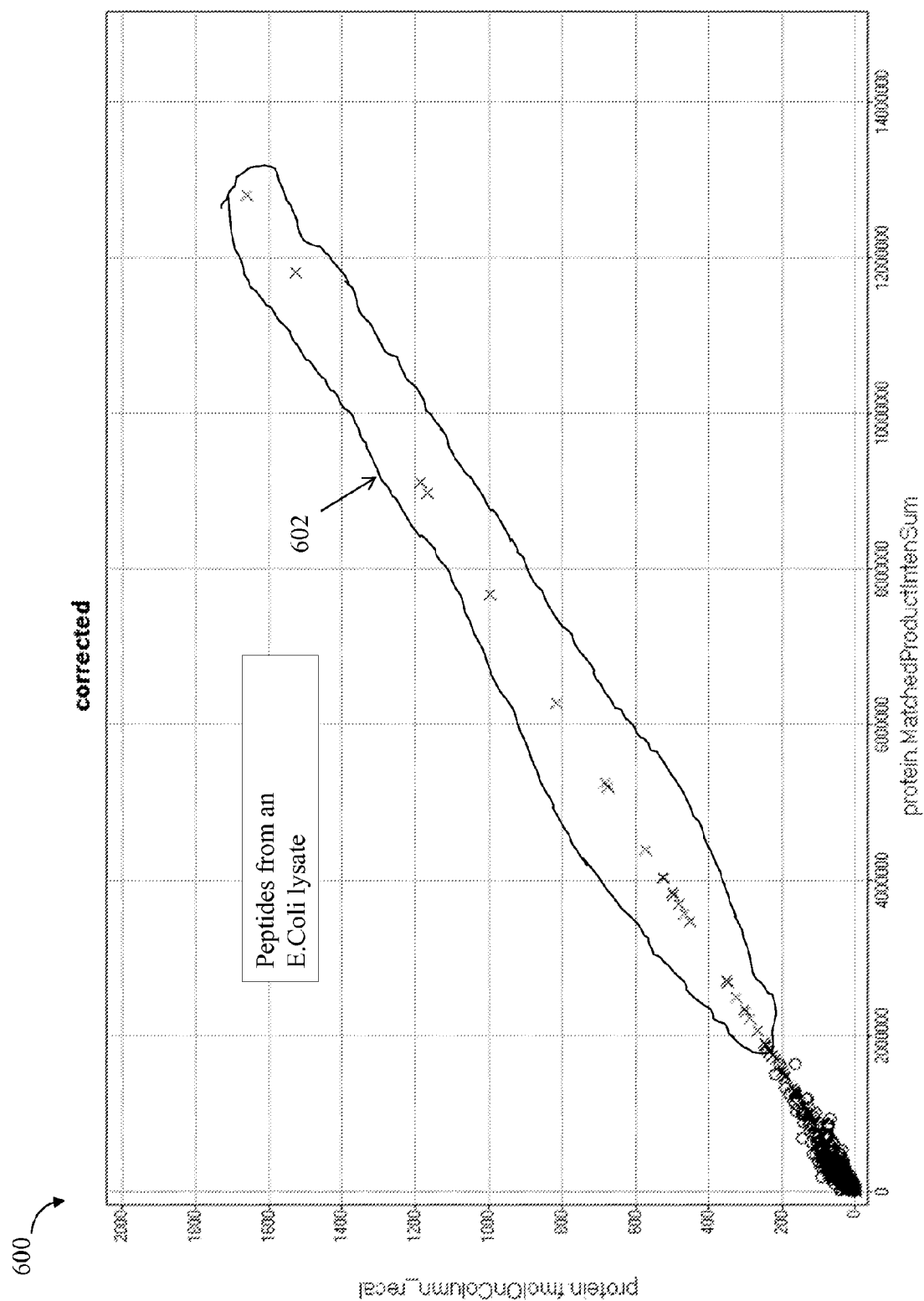
FIG. 6 is a graphical illustration including a version of corrected data from FIG. 5 as may be used in an embodiment in accordance with techniques herein.

Referring to FIG. 6, shown is an example graphically illustrating a corrected version of the data of FIG. 5 using the techniques herein. The example 600 illustrates data points of FIG. 5 which were characterized as non-linear as described above whereby such data points have been corrected to use adjusted or revised estimated molar amounts based on the summed product ion intensities for a protein rather than the summed precursor ion intensities. Element 602 generally represents, for example, corrected versions of data points included in 502 of FIG. 5. It should be noted that for each corrected data point, its X-axis value is the same in both FIGS. 5 and 6 and wherein the Y-axis value in FIG. 5 has been adjusted to that of the adjusted estimated molar amount as illustrated in FIG. 6. In connection with FIG. 6, it should be noted that the "X's" represent corrected values for those non-linear points denoted in FIG. 5. Those remaining points which are determined to otherwise be linear and not requiring such correction are denoted by "O" as in FIG. 5.

It should be noted that correction or adjustment of the non-linear points denoted as "X" in FIG. 5 may be adjusted or revised to a corrected point as in FIG. 6 using other techniques. For example, such correction may be determined by first examining data of FIG. 5 and performing linear curve fitting for those observed points having a linear response (e.g., thereby indicating responses or intensities within the detection saturation limit). Next, the molar amounts of those points designated as "X" (e.g., non-linear or otherwise indicating intensities exceeding the detection saturation limit) may be corrected or revised to have estimate molar amount by extrapolation using various parameters, such as regression parameters, obtained from linear curve fitting. Thus, multiple proteins may be used to determine the corrected or revised values for the non-linear points.

Thus, at or above the upper bound of the MS detection range (e.g., at or above the saturation point), our actual analyzed mass spectra data exhibits a non-linear response. Using the foregoing techniques as described, the actual MS data may be corrected for use with quantification of a protein at or above such a saturation point, or more generally, outside of the detector limits whereby such limits may be associated with a non-linear relationship exhibited in the uncorrected MS data such as illustrated in FIG. 5.

It should be noted that if there is 100% efficiency of fragmentation of a precursor ion, you would expect the sum of the intensities of the product ions associated with the precursor (e.g., where such fragments originate from the single precursor) to be equal to the sum of the precursor's intensity. However, systems typically do not exhibit such 100% efficiency but may be tuned to have, for example, approximately 90% fragmentation efficiency or some other desirable expected range of fragmentation efficiency. As such, the sum intensities of the product ions used in estimating the molar amount of a protein may be further upwardly adjusted or modified based on an expected or approximate fragmentation efficiency where the calibration standard uses precursor sum intensities of the top N precursor ionization intensities. For example, if the estimated fragmentation efficiency is 90% and the sum of the product ion intensities used to estimate the molar amount of a protein is 900, the foregoing sum of the product ion intensities may be increased to 1000 to account for the 90% fragmentation efficiency.

Figure 7:
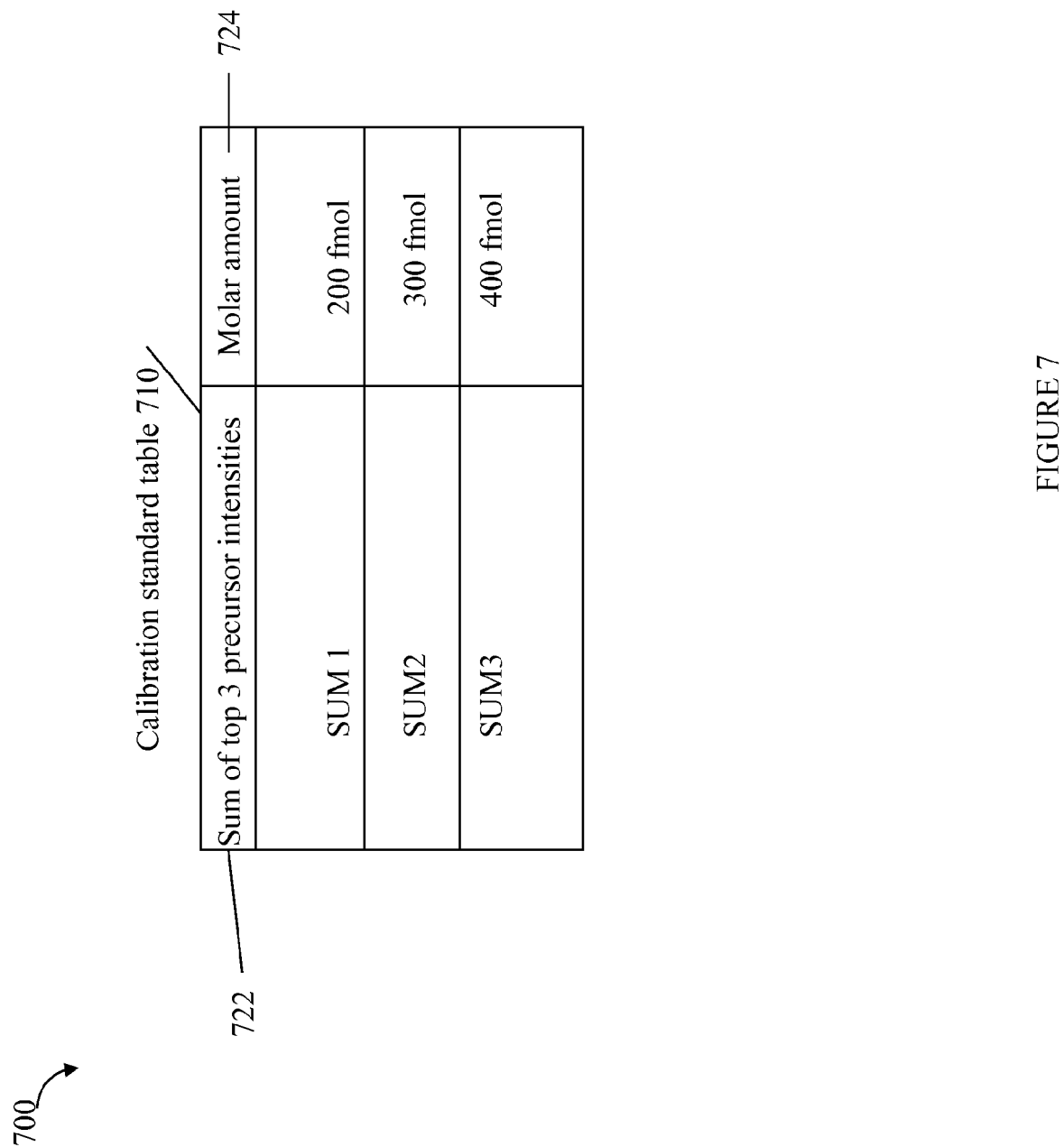

Referring to FIG. 7, shown is an example 700 illustrating a representation of a calibration table as may be used in connection with an embodiment in accordance with techniques herein. The '578 patent application describes a manner in which the calibration table containing precursor sum intensity data may be created. The calibration standard table 710 may be stored as a table of value pairs, each pair including a precursor sum intensity 722 (e.g., such as the sum of the top 3 precursor ionization intensities) for a protein and an associated molar amount 724 of the protein. Each such pair may be represented as a row in the table 710. The calibration standard may be obtained by performing sample analysis (e.g., LC-MS in a manner similar to that of samples described herein) using a calibration mixture of multiple known proteins at predetermined varying concentration amounts and recording the sum of the top 3 precursor ionization intensities associated with each such protein. Alternatively, the calibration standard may also be obtained using a calibration mixture of one or more known proteins at predetermined concentration amounts and recording the sum of the top 3 precursor ionization intensities associated with a particular protein. The foregoing may be repeated for the same such protein using varied known concentrations of the same particular protein. Thus, the calibration standard may be produced using varied known concentrations of the same protein and recording the precursor sum intensities of the top 3 precursors for the protein at each such known concentration. Alternatively, the calibration standard may be produced using such information for different proteins. The calibration standard is obtained using calibration sample mixtures known to result in ion intensities within the detection limits of the system utilized.

In the example 700, the calibration standard table may include 3 precursor intensity sums—SUM1 through SUM3—each associated with a different molar amount of a protein. The calibration standard table may be created and stored for use in estimating an amount of a protein which is the same or a different protein from that used in generating the calibration standard. For example, sample analysis may be performed for a mixture containing a particular protein by performing an LC-MS experiment and obtaining mass spectra. It may be desired to determine an absolute quantity of the particular protein. As such, the mass spectra may be analyzed to determine the sum of the top 3 precursor ionization intensities using the LE MS data and, for each such precursor, the sum of the top 3 product ions associated with each such precursor. The sum of the top 3 product ions may be obtained using the elevated or fragmentation scan data. It may be generally known that the concentration of the protein in the sample is high and expected to result in precursor ion intensities above the detection saturation limit. Alternatively, the observed precursor ion intensities of the mass spectra data may be in the general range or above a set intensity threshold indicative of the detector saturation limit. In this case, the molar amount of the protein may be estimated by summing the product ionization intensities of the top 3 product ions for each of the top 3 precursors (e.g., adding 9 product ionization intensities).

The foregoing product ionization intensity sum may be upwardly adjusted to account for an estimated fragmentation efficiency as described above. With reference to FIG. 7, the product ionization intensity sum may then be compared to the values in the column 722 of the calibration standard table 710. In this example, assume the values in the column 722 are stored in ascending order. Based on the comparison between the product ionization intensity sum and the values in column 722, there may be an exact match or it may be determined that the product ionization intensity sum falls between two of the values in two different rows. If there is an exact match (or a match within some threshold amount), for example, between the product ionization intensity sum and SUM1, the molar amount of the protein is estimated to be corresponding value in column 724 of 200 fmol. Alternatively, if the product ionization intensity sum is between the values of SUM 1 and SUM2, interpolation may be used to estimate the molar amount of the protein using corresponding values of 200 fmol and 300 fmol from column 724. For example, if the product ionization intensity sum is midway between SUM 1 and SUM2, the molar amount of the protein is estimated to be 250 fmol (e.g., midway between 200 fmol and 300 fmol) due to the linear relationship between the sum of the top 3 precursor intensities and the estimated molar amount (e.g., see the '578 patent application), the linear relationship between the sum of the top 3 precursor intensities and the sum of the top 3 product ionization intensities across the top 3 precursors (e.g., such as described herein and illustrated in FIG. 3), and therefore the linear relationship between the estimated molar amount and the sum of the top 3 product ionization intensities across the top 3 precursors (e.g., such as described herein and illustrated in FIG. 4).

It should be noted that although the calibration standard table is illustrated and described herein as including the sum of the top 3 precursor intensities for different molar amounts, the calibration standard table may alternatively, or additionally, include the sum of the top 3 product ion intensities for the foregoing top 3 precursors such as illustrated in FIG. 8.

Referring to FIG. 8, shown is an example of a calibration table 760 as may be produced and used in connection with techniques herein. The table 760 may be produced in a manner similar to that as described herein in connection with FIG. 7 and in the '578 patent application with the difference that the column 762 includes a sum of product ionization intensities for product ions associated with the top 3 precursors rather than the sum of the precursor ionization intensities for the foregoing top 3 precursors (as in 722 of FIG. 7). The values used in column 762 as sums of the product ionization intensities may be obtained by analyzing the mass spectra data of the high or elevated energy scans for product ions. For each precursor that has one of the top 3 precursor ionization intensities for a particular protein in a calibration mixture, the 3 product ions that are both associated with each such precursor that have the top 3 product ionization intensities may be summed and stored as a value in column 762 in the calibration standard table.

In this manner, when performing an experiment to estimate a molar amount of a protein in a sample using the product ionization sum of the protein's product ions (such as associated with the top 3 precursor ionization intensities observed for the protein), the product ionization sum observed for the protein may be compared to values of 762 in the calibration table 760 rather than values of 722 as in the calibration table 710. In such a case, it may be unnecessary to perform an adjustment to account for fragmentation efficiency if the fragmentation efficiency of the instruments used in determining the calibration table 760 is similar to the fragmentation efficiency of instruments used when estimating the molar amount of the protein in the experiment.

Figure 9:
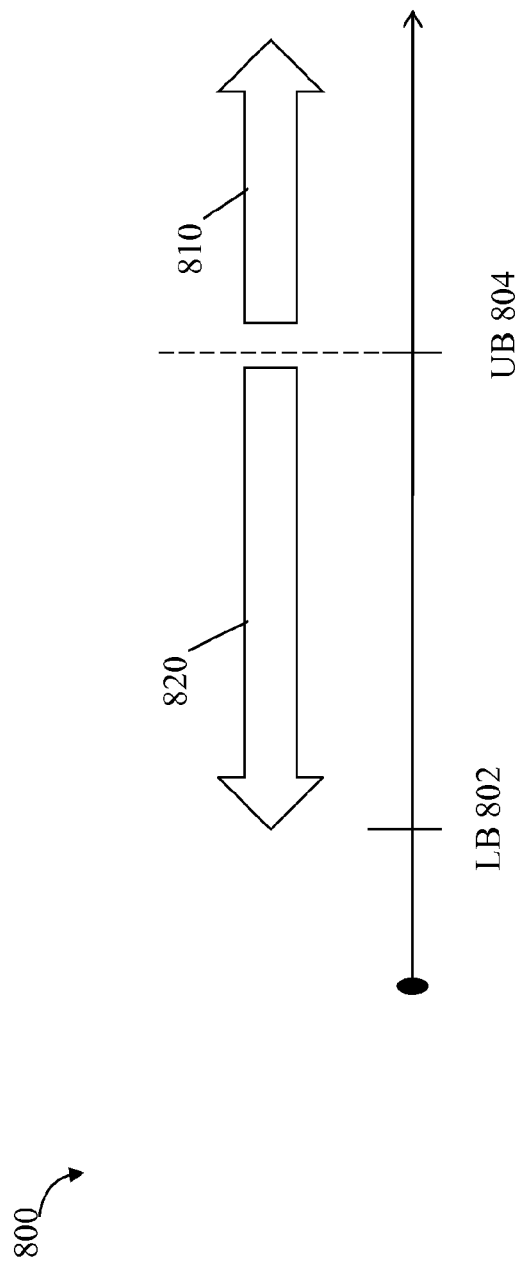
FIG. 9 is an example illustrating what observed ion intensity information may be used in estimating molar amounts of protein in an embodiment in accordance with techniques herein.

Referring to FIG. 9, shown is an example 800 illustrating what observed ion intensity information may be used in estimating molar amounts of protein in a sample in an experiment in accordance with the concentration or abundance of the protein and the detection range. The example 800 illustrates a dynamic range of a particular detector having a lower bound (LB) 802 and an upper bound (UB) 804. UB 804 is also referred to herein as the saturation limit or point at which the MS system may experience saturation effects. When it is determined that the particular protein in the experiment is expected to be present at a concentration having precursor ion intensities below the UB 804 (e.g., or within some specified tolerance of the UB 804), the sum of the precursor ionization intensities (e.g. such as of the N precursors having the top N precursor ionization intensities) observed for the protein may be used as described above and illustrated by 820 to estimate the molar amount of the protein. Otherwise, the sum of the product ionization intensities observed for the protein (e.g., sum of the top M product ionization intensities of product ions associated with each of the top N precursors, sum of M×N product ion intensities) may be used as described above and illustrated by 810 to estimate the molar amount of the protein. Thus, selection of whether to use observed intensities of precursor ions or product ions originating from a protein to estimate the molar quantity of the protein may be based on the intensity of such precursor ions. The saturation or detection limit may be determined or otherwise approximated in a variety of different ways. One way is by inspection of graphical observed data such as illustrated in FIG. 5 at a point where such data exhibits non-linearity. Another way is by knowledge of a particular instrument system as may be acquired through experimentation, based on limits or detections ranges provided by a vendor, and the like.

It should be noted that an embodiment is not restricted or otherwise limited to using the above-mentioned sum of product ionization intensities rather than the precursor ion intensities only in the particular instances as illustrated in FIG. 9. As will be appreciated by those of ordinary skill in the art, the sum of product ionization intensities may be generally used when practical and suitable such as when such product ion intensities do not approach the LB 802 of the detector range and/or are above some desired threshold. At very low concentrations, the fragments of a protein may not be detectable or above the lower detection limit of the MS system. Therefore, an embodiment in accordance with techniques herein may use a first set of observed precursor ion intensities to determine quantification of a protein where the precursor ion intensities are believed to be or known to be within the saturation limits of the system. Additionally, an embodiment in accordance with techniques herein may use observed fragment intensities associated with the precursors of the first set to determine quantification of a protein where the ionization intensities of such precursors are expected or known to be above the saturation limits of the detection range of the system.

Figure 10:
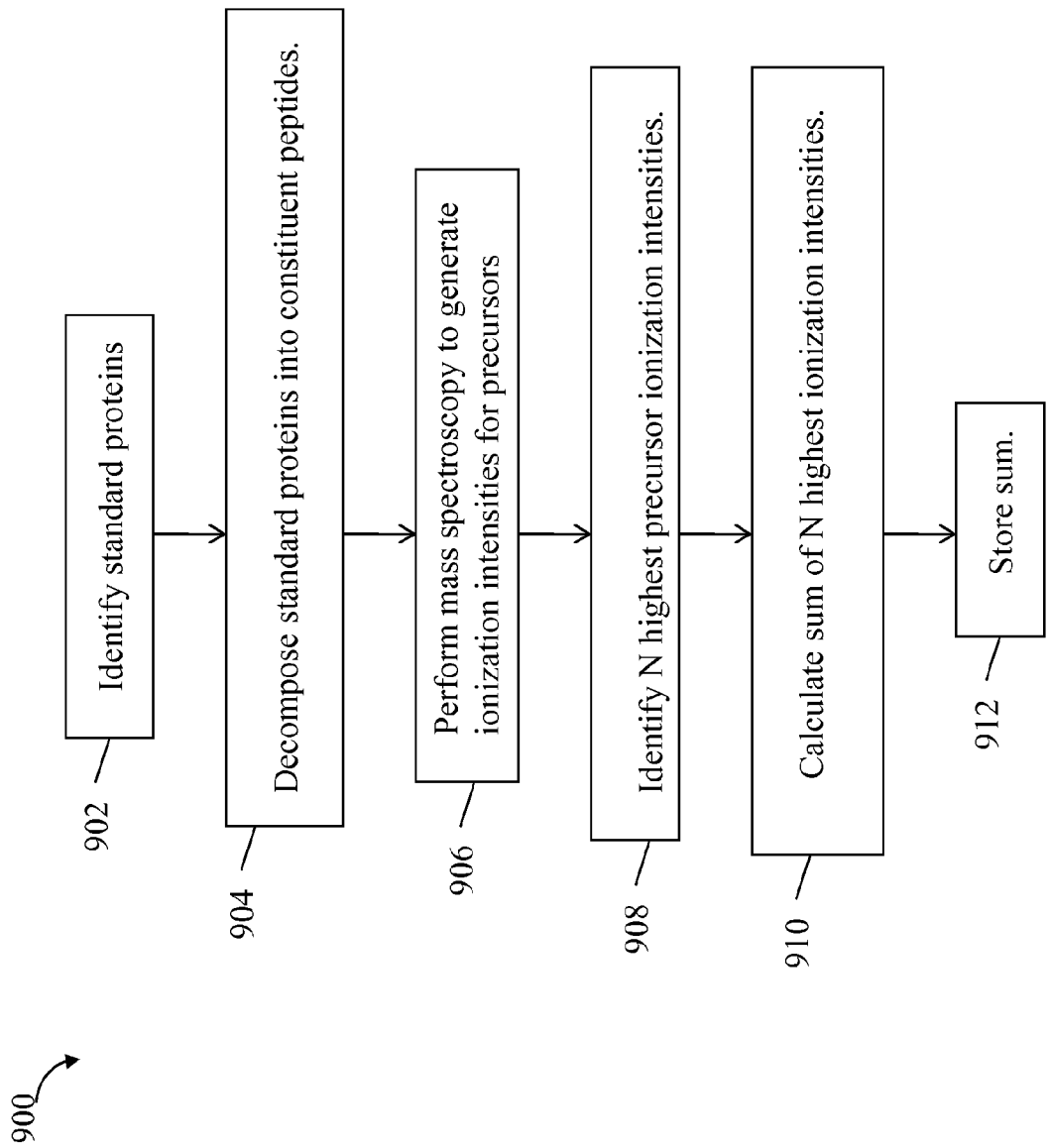
FIGS. 10, 11, 12, 13A and 13B are flowcharts of processing that may be performed in an embodiment in accordance with techniques herein.

Referring to FIG. 10, shown is an example of a flowchart of processing steps as may be used in an embodiment in accordance with techniques herein for generating a calibration standard table such as those described above and illustrated in FIGS. 7 and 8. In step 902, one or more calibration standard proteins to be used for a calibration standard are identified. In step 904, a known amount (such as in fmols or picomoles (pmols)) of each identified calibration standard protein may be decomposed to generate its constituent peptides. For example, such decomposition can be digestion using the enzyme trypsin. The known amount can also be obtained using prepared digests such as the MassPREP™ peptide digestion standards (available for proteins such as Phophrylase b, Yeast Enolase, Bovine Hemoglobin, Yeast Alcohol Dehydrogenase and Bovine Serum Albumin) available from Waters Corporation, Milford, Mass. In step 906, mass spectroscopic analysis is performed on the decomposition result. Step 906 may include performing analysis using LC/MS. In step 908, the N most efficiently ionizing precursors of peptides are identified. In step 910, the sum of the N most efficiently ionizing precursors or peptides is determined. In step 912, the sum is stored, for example, in a table such as the table of FIG. 7 along with the corresponding amount of protein. This process can be repeated for varying concentrations of protein. The table may also include the sum over all of the proteins, that is, a composite sum, for each of the concentrations in the table.

The foregoing processing of FIG. 10 may be repeated for a number of different amounts of the protein to generate a calibration standard table such as table 710 of FIG. 7. Although only one protein need be used for the calibration standard, averaging values for a plurality of selected calibration standard proteins is desirable to improve the statistics of the technique. The calibration standard table can also have only the average sum corresponding to each calibration standard protein, as well as optionally a covariance of the average sum. Any number of peptides can be used as the set of N most efficiently ionizing peptides. Using fewer than 3 however, may result in insufficient statistics to be accurate. As described, sums can be used to generate the calibration standards tables. Any one or more proteins can be used as the set of calibration standard proteins. Any one or more different amounts of protein can be used to generate the calibration standards tables. Using more proteins provides estimates on the coefficient of variation to provide additional confidence in subsequent analysis. Larger proteins having more peptides are likely to have more peptides showing higher ionizations as more peptides increase the likelihood of having amino acid sequences that result in higher ionization efficiency. Smaller proteins, which produce fewer tryptic peptides, are less likely to have many peptides with amino acid sequences indicative of high ionization efficiency. Consequently, N is likely to be able to be set higher when larger proteins are being analyzed.

Storage of calibration standard table precludes the need for regenerating the calibration standard table for each experiment. Moreover, the calibration standard table can be published or otherwise made available for others to use. For example, the table can be published in a journal or distributed by disk to interested users. Further, the table can be published on an Internet website, wherein distribution can be facilitated by a version of the table or tables that can be downloaded from the website. Numerous other methods for distributing such a calibration standard table would be well-known to those having skill in the art. Publication in this manner can be particularly advantageous wherein a particular user community agrees on one or more proteins to be used as the calibration standard. The calibration standard table also acts to provide a calibration for a particular instrument. That is, the calibration determines, for a specific instrument, the number of counts observed per molar amount for a given protein. This value may vary from instrument to instrument. However, once this value is determined through calibration, it is applicable to the absolute quantitation of all proteins generated from the particular instruments(s).

Figure 11:
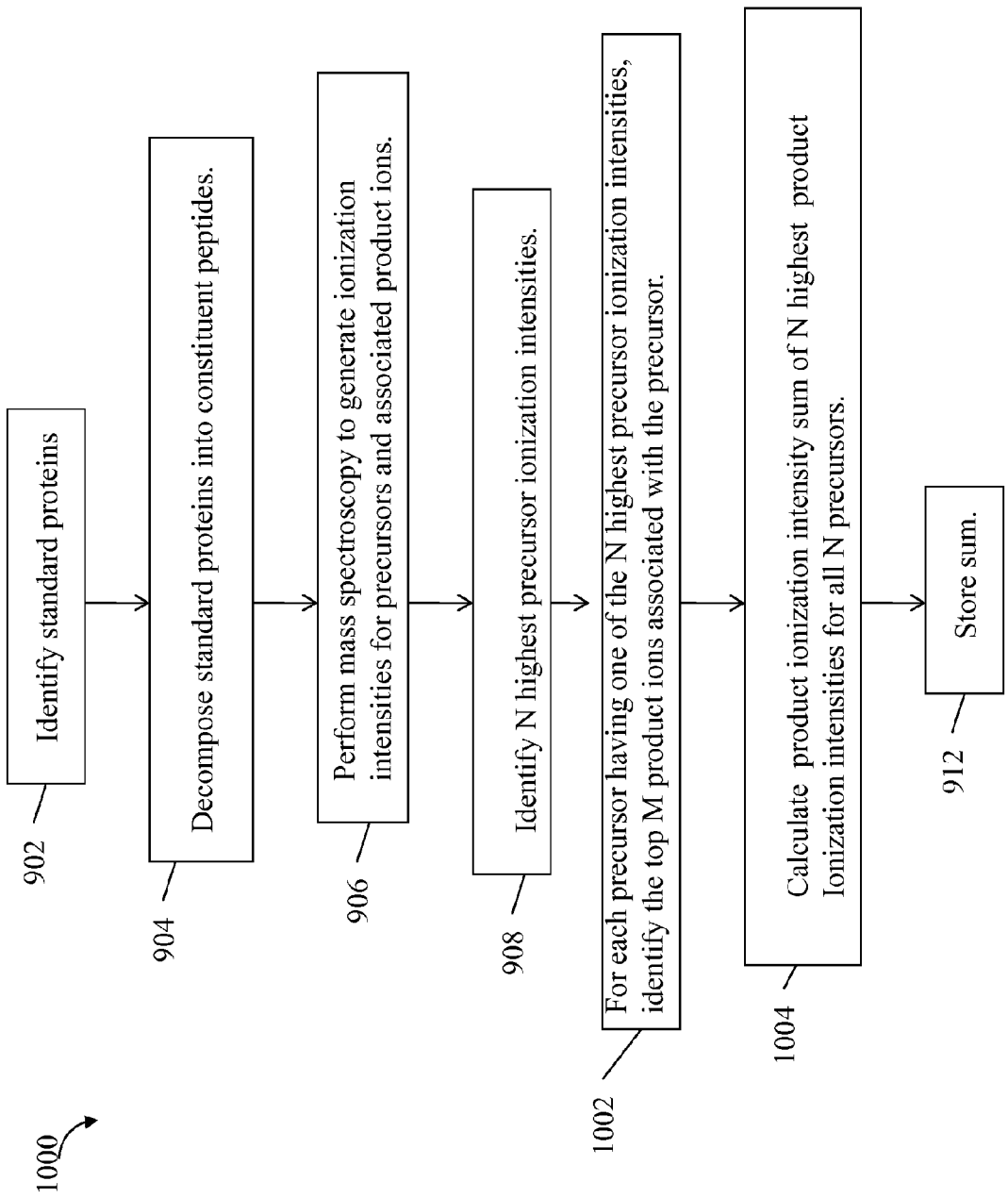

Referring to FIG. 11, shown is a flowchart of processing steps that may be used in an embodiment in connection with creating a calibration standard table for use in an embodiment in accordance with techniques herein. The flowchart 1000 outlines steps as may be performed to create a calibration table using product ion intensity sums such as for table 760 of FIG. 8. The flowchart 1000 of FIG. 11 includes steps 902, 904, 906 and 908 as described above in connection with FIG. 10. At step 1002, for each precursor having one of the N highest precursor ionization intensities, processing is performed to identify the top M product ions for the precursor. At step 1004, a product ionization intensity sum is calculated as the sum of the N highest product ionization intensities for all N precursors (having one of the top N precursor ionization intensities as determined in step 908). For example, if N and M are each 3, step 908 will add 9 product ion intensities (e.g., 3 product ion intensities are associated with product ions derived from each of the N precursors). At step 912, the foregoing sum of step 1004 is stored in a manner similar to that as described in connection with FIG. 10.

Although the calibration standard tables and observed ion intensities for precursors and product ions are described above as based on sums, as in the '578 patent application, an average intensity rather than a sum of intensities may alternatively be used in an embodiment.

An embodiment may also use a calibration table that is a combination of the foregoing (e.g., includes information of both tables 710 and 760). In this manner, the embodiment may use either precursor intensity information or product ion information when estimating a molar amount of a particular protein.

Figure 12:
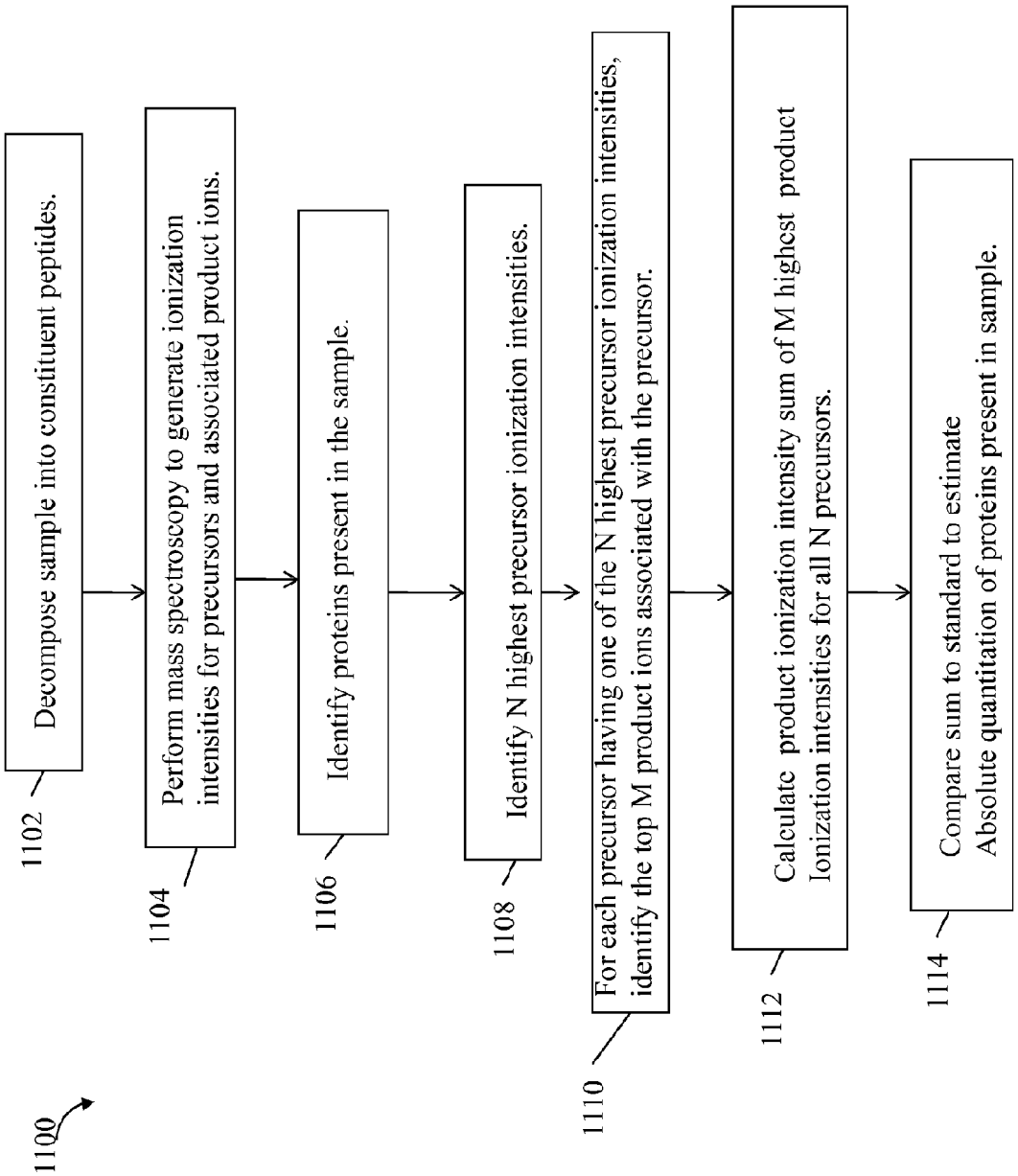

FIG. 12 is a flowchart of processing steps using a calibration standard table generated according to an embodiment such as described in FIGS. 10 and/or 11. The flowchart 1100 outlines steps utilizing product ion intensities for product ions originating from a protein to estimate the absolute quantity, such as molar quantity, of the protein in a sample.

In step 1102, a sample containing a protein or complex mixture of proteins is decomposed into its constituent peptides and run through the LCMS to collect the data. As above, the decomposition can be digestion using the enzyme Trypsin. In step 1104, mass spectroscopic analysis is performed on the decomposition result. In step 1106, proteins are identified. Step 1106 may be performed using any suitable technique known in the art. Step 1106 may include, for example, using a database containing information about known precursor and product ions for proteins and determining matches between precursor and product ion information in the database and observed mass spectra data. Matches may be made between different characteristics or parameters about the precursor and product ions such as mass and retention time (e.g., within specified tolerances). As known in the art, different techniques may be used in connection with identifying peptides and/or proteins based on a degree of matching between precursors and related product ions of an analyzed sample and those stored in a database containing information on known peptides and/or proteins. It should be noted that a database containing information used to identify proteins may be more generally any data store which may be used to store such information.

In step 1108, the N most efficiently ionizing peptides are identified for each protein identified in step 1106. In step 1110, for each precursor having one of the N highest precursor ionization intensities, identify the top M product ions associated with the precursor. At step 1112, a product ionization intensity sum is calculated for each protein as the sum of the M highest product ionization intensities for all N precursors (identified in step 1108 as having the top N precursor ionization intensities). In step 1114, the sum is compared to the calibration standard table such as table 760 of FIG. 8. Alternatively, step 1114 may compare the sum to the calibration standard table such as the table 710 of FIG. 7. In the latter instance where table 710 is used, the sum of step 1114 may be increased by an amount based on the fragmentation efficiency of the instrument utilized as described elsewhere herein. If the sum is present or matches an entry in the calibration table, then the corresponding amount of protein is used as the molar amount of the protein.

If the sum is not present in the calibration table, then the comparison includes calculating the absolute amount of protein based on the comparison. Such calculation can include linearly scaling the amounts in the calibration table based on a ratio of the sum determined in step 1112 and the intensities included in column 762 of FIG. 8. For example, if the sum determined in step 1112 for a protein is 100 and the sum included in an entry of 762 of table 760 is 200 having a corresponding molar amount of 200 fmols, then the estimated molar for the protein is 100 fmols due to the linear relationship between such values. Other techniques may be utilized such as other well-known interpolation techniques to estimate the molar amount of the protein based on the ion intensities in the calibration table. As with generating the standard tables, any number of peptides can be used as the set of N most efficiently ionizing peptides and any number of M product ions can be used. Using fewer than 3 for N and/or M however, may result in insufficient statistics to be accurate.

Figure 13A:
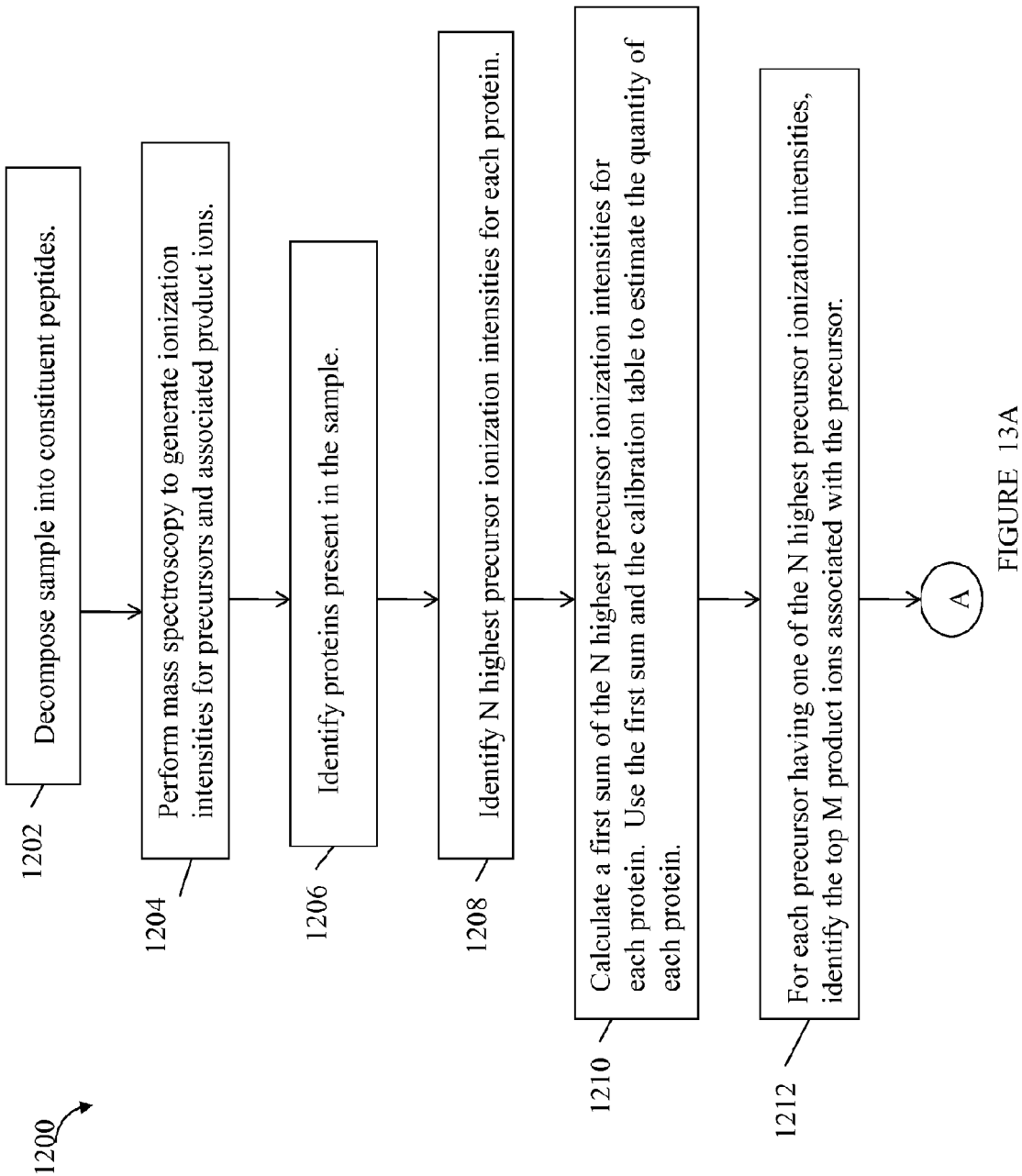
Figure 13B:
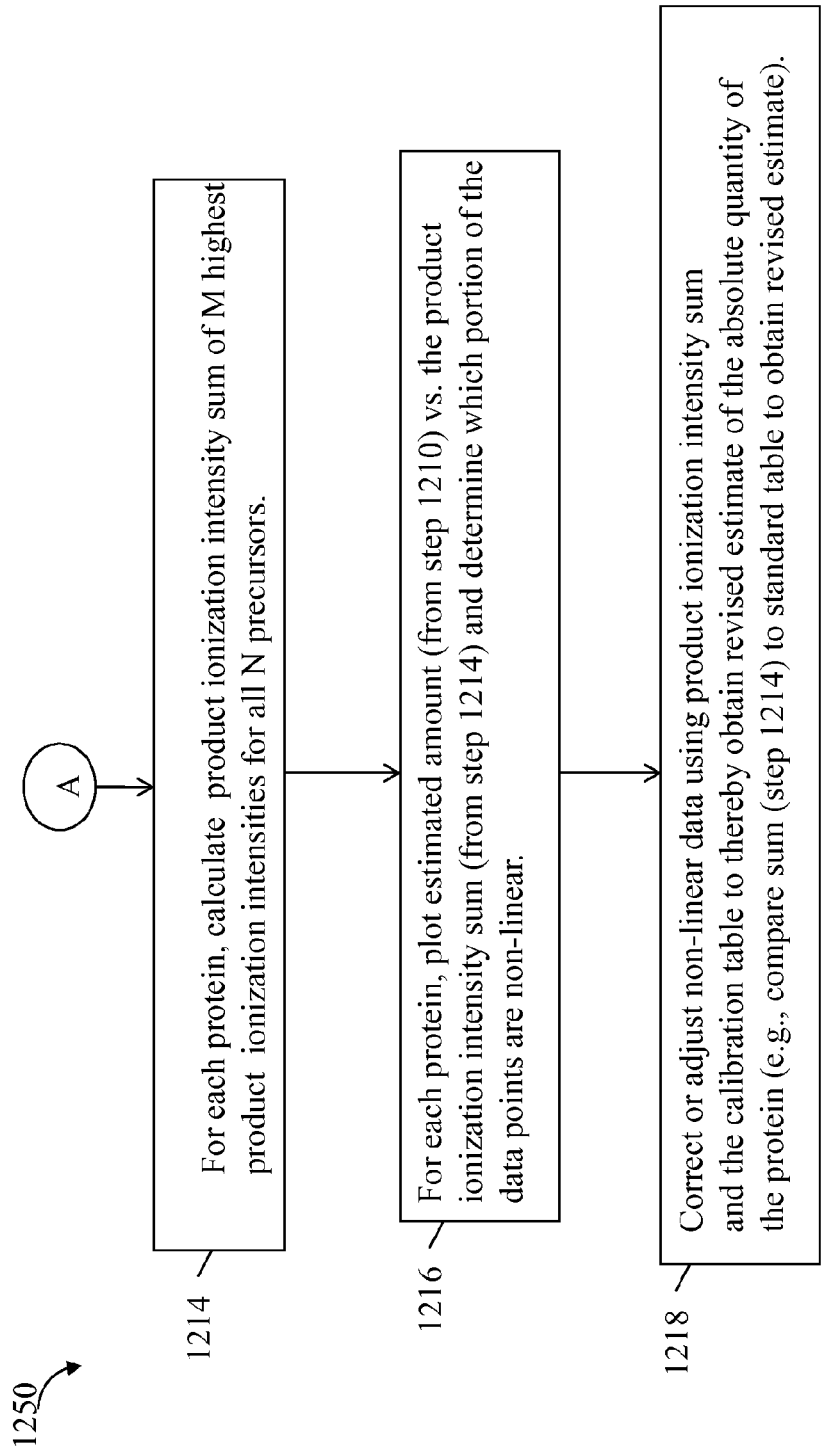

Referring to FIGS. 13A and 13B, shown is a flowchart of processing steps as may be used in an embodiment in accordance with techniques herein. Step 1202, 1204, 1206, and 1208 are similar, respectively, to steps 1102, 1104, 1106 and 1108 of FIG. 12. In step 1210, a first sum may be determined of the N highest precursor ionization intensities for each protein (e.g., as obtained in step 1108). The foregoing first sum and the calibration table (such as calibration table of FIG. 7) may be used to estimate the quantity of each protein. Step 1210 may perform processing as described herein and as also described in the '578 patent application to estimate the quantity of each protein. Step 1212 may be performed for each protein identified in step 1206. Steps 1212 and 1214 are respectively similar to step 1110 and 1112 of FIG. 11. In step 1216, for each protein, plot the estimated quantity (from step 1210) vs. the product ionization intensity sum (from step 1214) and determined which portion of the data points are non-linear. The plot such as a graphical representation may be as illustrated and described in connection with FIGS. 4 and 5. Using the foregoing data, plots may be generated to determine whether the data exhibits a linear relationship for example, as illustrated and described in connection with FIG. 4 or whether the data includes portions which are non-linear such as illustrated and described in connection with FIG. 5.

At step 1218, processing may be performed correct or adjust the non-linear data points using the product ionization intensity sum (from step 1214) and the calibration table to thereby obtain a revised estimate of the absolute quantity of the protein. Step 1218 may include comparing the sum from step 1214 to intensities in a calibrations standard table (e.g. FIG. 7 or 8) to obtain a revised estimate. For those data points which are linear, the estimated amount from step 1210. For those data points which are non-linear, the revised estimated quantity from step 1218 may be used.

Generally, techniques herein may be characterized as an improvement over the techniques of the '578 patent application where product ion intensities for product ions originating from a protein may be used to estimate the absolute quantity of the protein when precursor ion intensities of precursors originating from the protein exceed the detector saturation limit. Thus, in accordance with one aspect of the techniques herein, utilization of both precursor and product ion intensities may be used to extend the dynamic range of quantitative mass spectrometry experiments. The techniques herein may also be used as a means to estimate the molar amount of a protein in those instances where detector saturation occurs due to the intensity of the precursor ions.

As described above, such as in connection with step 1216 of FIG. 13B, data may be visually inspected or otherwise analyzed to determine which data points are non-linear thereby indicating which estimated molar amounts determined using precursor ion intensities are actually underestimates due to the precursor ion intensities being at or above the saturation limit. Alternatively, rather than identify which data points are non-linear as a means for determining whether to use estimated protein quantities obtained using precursor ionization intensities or product ionization intensities, an embodiment may have a set intensity threshold whereby when precursor ionization intensities are at or above this threshold (e.g. indicating of the saturation limit), the product ionization intensities are used rather than precursor ionization intensities to estimate the absolute quantity of the protein. Otherwise, the precursor ionization intensities of product ions originating from the protein are used to estimate the absolute quantity of the protein.

The techniques herein may also be utilized in connection with isotope labeled compounds. Isotopic labeling is a technique for tracking the passage of a sample of substance through a system. The substance is 'labeled' by including unusual isotopes in its chemical composition. If these unusual isotopes are later detected in a certain part of the system, they must have come from the labeled substance. One way to detect the presence of labeling isotopes is using mass spectrometry. Since isotopes have different masses the may be separated using mass spectrometry. As such, the techniques herein may be used to run two samples at once during a single experiment and label one of the samples using an isotope. A set mass difference between the samples due to the isotope labeling may be used to indicate relative quantitative changes between proteins of the two samples. In such a case, the fragment ions can be used to conduct relative quantification which represents the relative change in concentration of the proteins of the samples that are compared.

An embodiment in accordance with techniques herein may also use the estimated quantity of a protein determined using the product ionization intensities with the calibration table as a way to confirm another estimated quantity of the protein determined using the precursor ionization intensities.

It should be noted that, although preceding paragraphs and exemplary embodiments apply the techniques described herein generally to peptides and proteins, the techniques herein are also well suited for use with any other molecules including, but not limited to metabolites, lipids, sugars, pesticides, natural products, other organic species, and the like.

Exemplary embodiments are described utilizing techniques herein. Those of ordinary skill in the art will appreciate variations and other embodiments in which the techniques described herein may be also be utilized. For example, with reference back to FIG. 2A, the MS 212 may be generally any type of mass spectrometer and any configuration of components thereof. Additionally, as may be suitable for the particular sample, the MS may be used alone, or in combination with the LC or other separation means. Furthermore, and more generally, the processing may include the MS alone, or in combination with one or more other means of separation as may be suitable for use with the particular sample and associated complexity. For example, such as described in connection with FIGS. 1 and 2A above, the processing of a complex protein sample may include performing digestion processing in combination with LC and MS processing. As another illustration, processing may include performing ion mobility spectrometry alone, or in combination with, mass spectrometry and any other desired and/or suitable processing for sample analysis such as in connection with quantification of different molecules or analytes in a sample. For example, in one embodiment in accordance with techniques herein, ion mobility spectrometry may be performed prior to mass spectrometry.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method of performing protein quantification comprising:
   receiving ionization intensities for precursor ions and product ions detected in an experiment that analyzes a sample including a known concentration or quantity of a predetermined protein, said precursor ions and said product ions originating from the predetermined protein in the sample, wherein the ionization intensities are generated from performing the experiment including performing liquid chromatography and mass spectrometry;
   determining a first set of M precursor ions originating from the predetermined protein, wherein the first set of M precursor ions have the M highest ionization intensities of the precursor ions originating from the predetermined protein;
   determining, for each of the M precursor ions in the first set, a second set of N product ions that are fragments obtained by fragmentation of said each precursor ion, wherein the second set of N product ions have the N highest ionization intensities of product ions that are fragments obtained by fragmentation of said each precursor ion;
   calculating an intensity sum for the predetermined protein by adding ionization intensities of product ions included in the second sets for the M precursor ions in the first set;
   determining, in accordance with the known concentration or quantity of the predetermined protein in the sample and the intensity sum, information included in a calibration standard;
   performing a subsequent sample analysis using the calibration standard; and
   determining, using the calibration standard and subsequent experimental data obtained from the subsequent sample analysis, a quantity of a protein in another sample analyzed in the subsequent sample analysis.

2. The method of claim 1, wherein said calculating further includes:
   determining M product intensity sums, one of said M product intensity sums being determined for each of the M precursor ions of the first set by adding the N highest ionization intensities for the N product ions included in the second set for said each precursor ion; and
   determining said intensity sum by adding said M product intensity sums.

3. The method of claim 2, wherein M is equal to or greater than 3.

4. The method of claim 2, wherein N is equal to or greater than 3.

5. The method of claim 1, further comprising performing first processing including:
   obtaining a calibration standard mixture including a known concentration or quantity of a second predetermined protein;
   performing sample analysis including performing a second experiment using the calibration standard mixture, said second experiment including performing liquid chromatography and mass spectrometry with respect to the sample, said second experiment producing precursor ions and product ions, said sample analysis including obtaining ionization intensities for precursor ions and product ions originating from the second predetermined protein in the calibration standard mixture;
   determining a third set of M precursor ions originating from the second predetermined protein, wherein the third set of M precursor ions have the M highest ionization intensities of the precursor ions originating from the second predetermined protein;
   determining, for each of the M precursor ions in the third set for the predetermined protein, a fourth set of N product ions that are fragments obtained by fragmentation of said each precursor ion, wherein the fourth set of N product ions have the N highest ionization intensities of product ions that are fragments obtained by fragmentation of said each precursor ion;
   calculating an intensity sum for the second predetermined protein by adding ion intensities of product ions included in the fourth sets for the M precursors in the third set;
   storing a set of values included in the calibration standard, the set of values including a first value denoting the known concentration or quantity of the second predetermined protein and a second value denoting the intensity sum for the predetermined protein.

6. The method of claim 5, wherein said first processing is repeated for the second predetermined protein using a plurality of different known concentrations of the second predetermined protein.

7. The method of claim 5, wherein said first processing is repeated for one or more additional predetermined proteins.

8. The method of claim 5, wherein said calculating the intensity sum for the second predetermined protein further includes:
   determining M product intensity sums for the second predetermined protein, one of said M product intensity sums for the second predetermined protein being determined for each of the M precursor ions of the third set for the second predetermined protein by adding the N highest ionization intensities for the N product ions included in the fourth set for said each precursor ion; and
   determining said intensity sum for the second predetermined protein by adding said M product intensity sums for the second predetermined protein.

9. The method of claim 1, wherein the calibration standard includes a first plurality of value sets, each of the first plurality of value sets obtained by performing sample analysis of a calibration standard mixture including a known concentration of a first predetermined protein, said sample analysis including performing liquid chromatography and mass spectrometry, each of said value sets included in the first plurality comprising a first value denoting a first known concentration of the first predetermined protein and a second value denoting a first sum of an M highest ionization intensities for precursor ions originating from the first predetermined protein at the first known concentration.

10. The method of claim 9, further comprising:
    adjusting the first sum of at least one of the first plurality of value sets of the calibration standard.

11. The method of claim 1, wherein the calibration standard includes first information about precursor ion intensities at known concentrations for the at least one predetermined protein and second information about product ion intensities at known concentrations for the at least one predetermined protein.

12. The method of claim 11, wherein the first information of the calibration standard is used in said determining the quantity of the protein in the another sample when an abundance of the protein in the another sample, as indicated by precursor ion intensities of precursor ions originating from the protein, is not expected to exceed an upper bound of a detection limit of a mass spectrometer used to perform mass spectrometry in the subsequent sample analysis, and otherwise the second information of the calibration standard is used in said determining the quantity of the protein.

13. The method of claim 1, wherein the quantity of the protein is a molar amount.

14. The method of claim 1, further comprising:
receiving second ionization intensities for precursor ions and product ions detected in a second experiment that analyzes a second sample including a plurality of different proteins at varying concentrations, said precursor ions and said product ions originating from the plurality of different proteins in the second sample;
for each of the plurality of different proteins, determining a precursor intensity sum of an N highest ionization intensities of the second ionization intensities associated with N precursor ions originating from said each protein, and determining a product intensity sum by adding, for each of the N precursor ions, an M highest product ionization intensities of the second ionization intensities for product ions obtained by fragmentation of said each precursor ion;
determining an estimated molar amount of each of the plurality of different proteins using the calibration standard and the precursor intensity sum for said each protein, said calibration standard including one or more ionization intensities for one or more corresponding known concentrations or quantities of one or more predetermined proteins, wherein the estimated molar amount of said each protein for the precursor intensity sum of said each protein is determined in accordance with a first linear relationship between the one or more ionization intensities and the one or more corresponding known concentrations or quantities of the one or more predetermined proteins;
determining which one or more data points included in a plurality of data points do not exhibit a linear relationship between the estimated molar amounts and the product intensity sums determined for each of the plurality of different proteins, each of said plurality of data points representing the estimated molar amount and the product intensity sum for one of the plurality of different proteins; and
for each data point associated with one of the plurality of different proteins that does not exhibit the linear relationship thereby indicating that the estimated molar amount for the one protein does not vary linearly with respect to the product intensity sum for said one protein, determining a revised data point representing an adjusted estimated molar amount of said one protein for the product intensity sum of said each data point, wherein said product intensity sum for said each data point and said calibration standard are used to determine the adjusted estimated molar amount of said one protein for the revised data point in accordance with the linear relationship.

15. The method of claim 14, wherein the calibration standard includes a plurality of value sets, each of the plurality of value sets obtained by performing sample analysis of a calibration standard mixture including a known concentration of a particular predetermined protein, said sample analysis including performing liquid chromatography and mass spectrometry, each of said plurality of value sets included in the calibration standard comprising a first value denoting a known concentration in terms of a molar amount of the particular predetermined protein and a second value denoting a first sum of an N highest ionization intensities for precursor ions originating from the particular predetermined protein at the known concentration.

16. The method of claim 15, wherein using said product intensity sum and said calibration standard to determine the adjusted estimated molar amount of said one protein includes adjusting, in accordance with fragmentation efficiency, any of said product intensity sum for said each data point and one of the first values included in the plurality of value sets of the calibration standard.

17. The method of claim 15, wherein determining an estimated molar amount of each of the plurality of different proteins using a calibration standard and the precursor intensity sum for said each protein includes comparing the precursor intensity sum to one or more of the second values included in the plurality of value sets of the calibration standard.

18. The method of claim 17, wherein determining the estimated molar amount for at least one of the plurality of different proteins includes performing interpolation using two of said plurality of value sets in the calibration standard.

19. The method of claim 16, wherein using said product intensity sum of said each data point and said calibration standard to determine the adjusted estimated molar amount of said one protein further includes:
adjusting the product intensity sum of said each data point in accordance with fragmentation efficiency to determine an adjusted product intensity sum;
comparing the adjusted product intensity sum to one of the second values included in one of the plurality of value sets of the calibration standard; and
determining the adjusted estimated molar amount using the first value included in the one value set of the calibration standard.

20. The method of claim 14, wherein said second experiment includes performing digestion processing prior to performing liquid chromatography and mass spectrometry using the second sample.

21. The method of claim 20, wherein said digestion processing includes digesting at least one protein into precursor polypeptides through use of one or more enzymes or chemical cleavage.

22. The method of claim 14, wherein said second experiment further comprises performing ion mobility spectrometry.

23. A method of performing quantification comprising:
receiving ionization intensities for precursor ions and product ions detected in an experiment that analyzes a sample including a known concentration of quantity of a predetermined molecule, said precursor ions and said product ions originating from the predetermined molecule in the sample, wherein the ionization intensities are generated from performing the experiment comprising performing liquid chromatography and mass spectrometry;
determining a first set of one or more precursor ions originating from the predetermined molecule, wherein the first set of one or more precursor ions have highest ionization intensities of the precursor ions originating from the predetermined molecule;

determining, for each of the one or more precursor ions in the first set, a second set of one or more product ions that are fragments obtained by fragmentation of said each precursor ion, wherein the second set of one or more product ions have highest ionization intensities of product ions that are fragments obtained by fragmentation of said each precursor ion;

calculating an intensity sum for the predetermined molecule by adding ionization intensities of product ions included in the one or more second sets for the one or more precursor ions in the first set;

determining, in accordance with the known concentration or quantity of the predetermined molecule in the sample and the intensity sum, information included in a calibration standard;

performing a subsequent sample analysis using the calibration standard; and determining, using the calibration standard and subsequent experimental data obtained from the subsequent sample analysis, a quantity of a molecule in another sample analyzed in the subsequent sample analysis.

24. The method of claim 1, wherein the calibration standard includes one or more ionization intensities for one or more corresponding known concentrations or quantities of one or more predetermined proteins, and wherein said subsequent experimental data includes ionization intensities for precursor ions and product ions originating from the protein in the another sample, and wherein said determining the quantity of the protein in the another sample further includes:

determining a third set of M precursor ions originating from the protein, wherein the third set of M precursor ions have the M highest ionization intensities of the precursor ions originating from the protein;

determining, for each of the M precursor ions in the third set for the protein, a fourth set of N product ions that are fragments obtained by fragmentation of said each precursor ion, wherein the fourth set of N product ions have the N highest ionization intensities of product ions that are fragments obtained by fragmentation of said each precursor ion;

calculating a second intensity sum for the protein by adding ion intensities of product ions included in the fourth sets for the M precursors in the third set;

comparing the second intensity sum for the protein to at least a first ionization intensity of the one or more ionization intensities included in the calibration standard; and determining the quantity of the protein in the another sample based on said comparing.

25. The method of claim 24, wherein said determining the quantity of the protein in the another sample further includes:

determining whether the second intensity sum matches the first ionization intensity in the calibration standard, said first ionization intensity having a first of the one or more corresponding known concentrations or quantities; and responsive to determining the second intensity sum matches the first ionization intensity value in the calibration standard, estimating the quantity of the protein to be the first corresponding known concentration or quantity.

26. The method of claim 25, wherein said determining the quantity of the protein in the another sample further includes:

determining whether the second intensity sum matches any of the one or more ionization intensities in the calibration standard; and responsive to determining the second intensity sum does not match any of the one or more ionization intensities in the calibration standard, estimating the quantity of the protein based on a linear relationship between the one or more ionization intensities in the calibration standard and the one or more corresponding known concentrations or quantities of the one or more predetermined proteins.

27. The method of claim 26, wherein said estimating includes linearly scaling at least one of the one or more ionization intensities in the calibration standard and linearly scaling at least one of the one or more corresponding known concentrations or quantities.

28. The method of claim 26, wherein the one or more ionization intensities in the calibration standard including a plurality of ionization intensities for a plurality of corresponding known concentrations or quantities of one or more predetermined proteins, and wherein said estimating includes performing interpolation using two of the plurality of ionization intensities and two of the plurality of corresponding known concentrations or quantities.

29. The method of claim 14, wherein said determining an estimated molar amount of each of the plurality of different proteins comprises:

comparing the precursor sum for said each protein to at least a first ionization intensity of the one or more ionization intensities of the calibration standard; and determining the estimated molar amount for said each protein based on said comparing the precursor sum.

30. The method of claim 1, wherein said determining a first set, said determining a second set, said calculating, said determining information included in the calibration standard, and said determining a quantity are performed using one or more processors.

31. The method of claim 14, wherein said determining a precursor sum intensity, said determining an estimated molar amount of each of the plurality of proteins, said determining which one or more data points, and said determining a revised data point are performed using one or more processors.

32. The method of claim 23, wherein said determining a first set, said determining a second set, said calculating, said determining information included in the calibration standard, and said determining a quantity are performed using one or more processors.

33. A system comprising:

a chromatography module that performs liquid chromatography;

a mass spectrometer that performs perform mass spectrometry; and a memory comprising code stored therein that, when executed by a processor, performs a method of protein quantification comprising:

receiving ionization intensities for precursor ions and product ions detected in an experiment that analyzes a sample including a known concentration or quantity of a predetermined protein, said precursor ions and said product ions originating from the predetermined protein in the sample, wherein the ionization intensities are generated from performing the experiment including performing liquid chromatography using the chromatography module and mass spectrometry using the mass spectrometer;

determining a first set of M precursor ions originating from the predetermined protein, wherein the first set of M precursor ions have the M highest ionization intensities of the precursor ions originating from the predetermined protein;

determining, for each of the M precursor ions in the first set, a second set of N product ions that are fragments obtained by fragmentation of said each precursor ion, wherein the second set of N product ions have the N highest ionization intensities of product ions that are fragments obtained by fragmentation of said each precursor ion;

calculating an intensity sum for the predetermined protein by adding ionization intensities of product ions included in the second sets for the M precursor ions in the first set;

determining, in accordance with the known concentration or quantity of the predetermined protein in the sample and the intensity sum, information included in a calibration standard;

performing a subsequent sample analysis using the calibration standard; and determining, using the calibration standard and subsequent experimental data obtained from the subsequent sample analysis, a quantity of a protein in another sample analyzed in the subsequent sample analysis.

34. A system comprising:

a chromatography module that performs liquid chromatography;

a mass spectrometer that performs perform mass spectrometry; and a memory comprising code stored therein that, when executed by a processor, performs a method of quantification of molecules comprising:

receiving ionization intensities for precursor ions and product ions detected in an experiment that analyzes a sample including a known concentration of quantity of a predetermined molecule, said precursor ions and said product ions originating from the predetermined molecule in the sample, wherein the ionization intensities are generated from performing the experiment comprising performing liquid chromatography using the chromatography module and mass spectrometry using the mass spectrometer;

determining a first set of one or more precursor ions originating from the predetermined molecule, wherein the first set of one or more precursor ions have highest ionization intensities of the precursor ions originating from the predetermined molecule;

determining, for each of the one or more precursor ions in the first set, a second set of one or more product ions that are fragments obtained by fragmentation of said each precursor ion, wherein the second set of one or more product ions have highest ionization intensities of product ions that are fragments obtained by fragmentation of said each precursor ion;

calculating an intensity sum for the predetermined molecule by adding ionization intensities of product ions included in the one or more second sets for the one or more precursor ions in the first set;

determining, in accordance with the known concentration or quantity of the predetermined molecule in the sample and the intensity sum, information included in a calibration standard;

performing a subsequent sample analysis using the calibration standard; and determining, using the calibration standard and subsequent experimental data obtained from the subsequent sample analysis, a quantity of a molecule in another sample analyzed in the subsequent sample analysis.

35. The system of claim 34, further comprising an instrument that perform ion mobility spectrometry.

36. The system of claim 34, wherein the another sample is a mixture including a plurality of proteins.

37. The system of claim 34, wherein the molecule is any of a protein, lipid, metabolite, and an organic molecular species.

* * * * *